United States Patent
Fisher et al.

(10) Patent No.: US 9,572,588 B2
(45) Date of Patent: Feb. 21, 2017

(54) DYNAMIC KNEE BALANCER WITH FORCE OR PRESSURE SENSING

(71) Applicant: Synvasive Technology, Inc., El Dorado Hills, CA (US)

(72) Inventors: Michael Fisher, Folsom, CA (US); Anthony K Hedley, Paradise Valley, AZ (US); Michael Howard, Scottsdale, AZ (US); Kevin M Cordes, Placerville, CA (US); Toshinobu Katsuya, Kobe (JP)

(73) Assignee: Synvasive Technology, Inc., El Dorado Hills, CA (US)

( * ) Notice: Subject to any disclaimer, the term of this patent is extended or adjusted under 35 U.S.C. 154(b) by 334 days.

(21) Appl. No.: 13/709,506

(22) Filed: Dec. 10, 2012

(65) Prior Publication Data
US 2013/0096567 A1    Apr. 18, 2013

Related U.S. Application Data

(60) Continuation of application No. 12/511,527, filed on Jul. 29, 2009, now Pat. No. 8,715,290, which is a
(Continued)

(51) Int. Cl.
*A61B 17/56* (2006.01)
*A61B 17/16* (2006.01)
(Continued)

(52) U.S. Cl.
CPC ......... *A61B 17/1626* (2013.01); *A61F 2/4657* (2013.01); *A61F 2/4684* (2013.01); *A61F 2/38* (2013.01); *A61F 2002/4666* (2013.01)

(58) Field of Classification Search
CPC .............................. A61B 17/154; A61B 17/155
See application file for complete search history.

(56) References Cited

U.S. PATENT DOCUMENTS

| 4,211,228 A | 7/1980 | Cloutier |
| 4,220,146 A | 9/1980 | Cloutier |

(Continued)

FOREIGN PATENT DOCUMENTS

| CA | 2555283 C | 7/2014 |
| EP | 979636 A2 | 2/2000 |

(Continued)

OTHER PUBLICATIONS

"U.S. Appl. No. 12/511,527, Notice of Allowance mailed Dec. 18, 2013", 18 pgs.

(Continued)

*Primary Examiner* — Mary Hoffman
(74) *Attorney, Agent, or Firm* — Schwegman Lundberg & Woessner, P.A.

(57) ABSTRACT

A device for performing a surgical procedure on a knee includes an adjustable femoral portion, a tibial portion and at least one sensor coupled with the femoral and/or tibial portions to sense pressure exerted by the femoral and tibial portions against one another. The femoral portion is adapted for removably coupling with a distal end of a femur to adjust tension in soft tissue adjacent the knee and has at least one positioning feature adapted to move relative to the distal end of the femur as the femoral portion is adjusted, thus helping position a femoral prosthetic on the distal end of the femur. The sensor(s) may be adapted to sense pressure at medial and lateral sides of the knee, and relative pressures may be displayed as data on a visual display. Adjustments to the femoral member may be made to balance pressure at flexion and extension of the knee.

23 Claims, 15 Drawing Sheets

Related U.S. Application Data division of application No. 10/973,936, filed on Oct. 25, 2004, now Pat. No. 7,578,821, which is a continuation-in-part of application No. 10/773,608, filed on Feb. 6, 2004, now Pat. No. 7,442,196.

(51) Int. Cl.
*A61F 2/46* (2006.01)
*A61F 2/38* (2006.01)

(56) References Cited

U.S. PATENT DOCUMENTS

| | | |
|---|---|---|
| 4,501,266 A | 2/1985 | McDaniel |
| 4,524,766 A | 6/1985 | Petersen |
| 4,567,886 A | 2/1986 | Petersen |
| 5,163,949 A | 11/1992 | Bonutti |
| 5,197,488 A | 3/1993 | Kovacevic |
| 5,207,711 A | 5/1993 | Caspari et al. |
| 5,344,461 A | 9/1994 | Phlipot |
| 5,360,016 A | 11/1994 | Kovacevic |
| 5,464,406 A | 11/1995 | Ritter et al. |
| 5,470,354 A | 11/1995 | Hershberger et al. |
| 5,489,311 A | 2/1996 | Cipolletti |
| 5,514,183 A | 5/1996 | Epstein |
| 5,520,695 A | 5/1996 | Luckman |
| 5,540,696 A | 7/1996 | Booth, Jr. et al. |
| 5,597,379 A | 1/1997 | Haines et al. |
| 5,630,820 A | 5/1997 | Todd |
| 5,649,929 A | 7/1997 | Callaway |
| 5,656,785 A | 8/1997 | Trainor et al. |
| 5,669,914 A | 9/1997 | Eckhoff |
| 5,688,282 A | 11/1997 | Baron et al. |
| 5,702,464 A | 12/1997 | Lackey et al. |
| 5,733,292 A | 3/1998 | Gustilo et al. |
| 5,735,904 A | 4/1998 | Pappas |
| 5,755,801 A | 5/1998 | Walker et al. |
| 5,782,925 A | 7/1998 | Collazo et al. |
| 5,800,438 A | 9/1998 | Tuke et al. |
| 5,860,980 A | 1/1999 | Axelson, Jr. et al. |
| 5,879,394 A | 3/1999 | Ashby et al. |
| 5,880,976 A | 3/1999 | DiGioia, III et al. |
| 5,911,723 A | 6/1999 | Ashby et al. |
| 6,022,377 A | 2/2000 | Nuelle et al. |
| 6,056,756 A | 5/2000 | Eng et al. |
| 6,068,658 A | 5/2000 | Insall et al. |
| 6,096,043 A | 8/2000 | Techiera et al. |
| 6,296,666 B1 | 10/2001 | Gardner |
| 6,361,564 B1 | 3/2002 | Marceaux et al. |
| 6,488,711 B1 | 12/2002 | Grafinger |
| 6,506,215 B1 | 1/2003 | Letot et al. |
| 6,558,427 B2 | 5/2003 | Leclercq et al. |
| 6,575,980 B1 | 6/2003 | Robie et al. |
| 6,632,225 B2 | 10/2003 | Sanford et al. |
| 6,648,896 B2 | 11/2003 | Overes et al. |
| 6,972,039 B2 | 12/2005 | Metzger et al. |
| 6,984,249 B2 | 1/2006 | Keller |
| 7,097,662 B2 | 8/2006 | Evans, III et al. |
| 7,101,401 B2 | 9/2006 | Brack |
| 7,442,196 B2 | 10/2008 | Fisher et al. |
| 7,575,602 B2 | 8/2009 | Amirouche et al. |
| 7,578,821 B2 | 8/2009 | Fisher et al. |
| 7,837,691 B2 | 11/2010 | Cordes et al. |
| 8,491,589 B2 | 7/2013 | Fisher et al. |
| 8,715,290 B2 | 5/2014 | Fisher et al. |
| 8,758,355 B2 | 6/2014 | Fisher et al. |
| 2002/0029045 A1 | 3/2002 | Bonutti |
| 2002/0052606 A1 | 5/2002 | Bonutti |
| 2002/0198530 A1 | 12/2002 | Sanford et al. |
| 2003/0028196 A1 | 2/2003 | Bonutti |
| 2003/0069644 A1 | 4/2003 | Kovacevic et al. |
| 2003/0130665 A1 | 7/2003 | Pinczewski et al. |
| 2003/0187452 A1 | 10/2003 | Smith et al. |
| 2004/0019382 A1 | 1/2004 | Amirouche et al. |
| 2004/0064073 A1 | 4/2004 | Heldreth |
| 2004/0064191 A1 | 4/2004 | Wasielewski |
| 2004/0167450 A1* | 8/2004 | Buckman et al. ............ 602/23 |
| 2004/0236424 A1 | 11/2004 | Berez et al. |
| 2005/0010302 A1 | 1/2005 | Dietz et al. |
| 2005/0119661 A1 | 6/2005 | Hodgson et al. |
| 2006/0081063 A1 | 4/2006 | Neubauer et al. |
| 2006/0241640 A1 | 10/2006 | Briard et al. |
| 2007/0198022 A1 | 8/2007 | Lang et al. |
| 2013/0013075 A1 | 1/2013 | Fisher et al. |
| 2013/0013076 A1 | 1/2013 | Fisher et al. |

FOREIGN PATENT DOCUMENTS

| | | |
|---|---|---|
| EP | 1402857 A2 | 3/2004 |
| EP | 1718232 B1 | 10/2012 |
| EP | 2567664 A2 | 3/2013 |
| EP | 2567665 A2 | 3/2013 |
| JP | H11513274 A | 11/1999 |
| JP | 2008517708 A | 5/2008 |
| KR | 1158952 | 6/2012 |
| WO | WO-9709939 A1 | 3/1997 |
| WO | WO-9832384 A1 | 7/1998 |

OTHER PUBLICATIONS

"U.S. Appl. No. 13/619,227, Notice of Allowance mailed Feb. 20, 2014", 5 pgs.
"U.S. Appl. No. 13/619,227, Preliminary Amendment filed Sep. 14, 2012", 3 pgs.
"U.S. Appl. No. 13/619,227, Supplementary Preliminary Amendment filed Sep. 24, 2012", 6 pgs.
"Canadian Application Serial No. 2,585,862, Office Action mailed Oct. 18, 2013", 4 pgs.
"Canadian Application Serial No. 2,585,862, Response filed Apr. 15, 2014 to Office Action mailed Oct. 18, 2013", 9 pgs.
"European Application Serial No. 12006956.2, Examination Notification Art. 94(3) mailed Apr. 14, 2014", 6 pgs.
"European Application Serial No. 12006956.2, Response filed Dec. 19, 2013 to Extended European Search Report mailed May 22, 2013", 7 pgs.
"U.S. Appl. No. 10/773,608, Advisory Action mailed Mar. 7, 2007", 3 pgs.
"U.S. Appl. No. 10/773,608, Examiner Interview Summary mailed Jul. 13, 2007", 4 pgs.
"U.S. Appl. No. 10/773,608, Examiner Interview Summary mailed Jul. 19, 2006", 3 pgs.
"U.S. Appl. No. 10/773,608, Examiner Interview Summary mailed Aug. 1, 2006", 4 pgs.
"U.S. Appl. No. 10/773,608, Final Office Action mailed Jun. 12, 2008", 5 pgs.
"U.S. Appl. No. 10/773,608, Final Office Action mailed Oct. 16, 2007", 10 pgs.
"U.S. Appl. No. 10/773,608, Final Office Action mailed Dec. 1, 2006", 8 pgs.
"U.S. Appl. No. 10/773,608, Non Final Office Action mailed Jan. 24, 2008", 6 pgs.
"U.S. Appl. No. 10/773,608, Non Final Office Action mailed Jun. 4, 2007", 9 pgs.
"U.S. Appl. No. 10/773,608, Non Final Office Action mailed Jun. 27, 2006", 10 pgs.
"U.S. Appl. No. 10/773,608, Notice of Allowance mailed Sep. 5, 2008", 9 pgs.
"U.S. Appl. No. 10/773,608, Response filed Feb. 12, 2008 to Non Final Office Action mailed Jan. 24, 2008", 11 pgs.
"U.S. Appl. No. 10/773,608, Response filed Feb. 13, 2007 to Final Office Action mailed Dec. 1, 2006", 17 pgs.
"U.S. Appl. No. 10/773,608, Response filed Apr. 12, 2006 to Restriction Requirement mailed Mar. 20, 2006", 22 pgs.
"U.S. Appl. No. 10/773,608, Response filed Jun. 18, 2008 to Final Office Action mailed Jun. 12, 2008", 10 pgs.
"U.S. Appl. No. 10/773,608, Response filed Jul. 19, 2007 to Non Final Office Action mailed Jun. 4, 2007", 17 pgs.
"U.S. Appl. No. 10/773,608, Response filed Sep. 15, 2006 to Non Final Office Action mailed Jun. 27, 2006", 24 pgs.

(56) References Cited

OTHER PUBLICATIONS

"U.S. Appl. No. 10/773,608, Response filed Oct. 29, 2007 to Final Office Action mailed Oct. 16, 2007", 12 pgs.
"U.S. Appl. No. 10/773,608, Restriction Requirement mailed Mar. 20, 2006", 6 pgs.
"U.S. Appl. No. 10/973,936, Final Office Action mailed Aug. 7, 2008", 5 pgs.
"U.S. Appl. No. 10/973,936, Non Final Office Action mailed Jan. 6, 2009", 6 pgs.
"U.S. Appl. No. 10/973,936, Non Final Office Action mailed Nov. 27, 2007", 7 pgs.
"U.S. Appl. No. 10/973,936, Notice of Allowance mailed Jul. 9, 2009", 4 pgs.
"U.S. Appl. No. 10/973,936, Response filed Mar. 18, 2009 to Non Final Office Action mailed Jan. 6, 2009", 8 pgs.
"U.S. Appl. No. 10/973,936, Response filed Mar. 27, 2008 to Non Final Office Action mailed Nov. 27, 2007", 10 pgs.
"U.S. Appl. No. 10/973,936, Response filed Aug. 31, 2007 to Restriction Requirement mailed Jul. 30, 2007", 5 pgs.
"U.S. Appl. No. 10/973,936, Response filed Oct. 7, 2008 to Final Office Action mailed Aug. 7, 2008", 8 pgs.
"U.S. Appl. No. 10/973,936, Restriction Requirement Jul. 30, 2007", 5 pgs.
"U.S. Appl. No. 11/149,944, Non Final Office Action mailed Dec. 29, 2009", 7 pgs.
"U.S. Appl. No. 11/149,944, Notice of Allowance mailed Jul. 12, 2010", 5 pgs.
"U.S. Appl. No. 11/149,944, Response filed Feb. 19, 2010 to Non Final Office Action mailed Dec. 29, 2009", 13 pgs.
"U.S. Appl. No. 12/511,527, Response filed May 15, 2013 to Final Office Action mailed Mar. 21, 2013", 14 pgs.
"U.S. Appl. No. 12/511,527, Advisory Action mailed Jun. 7, 2013", 3 pgs.
"U.S. Appl. No. 12/511,527, Appeal Brief filed Aug. 20, 2013", 16 pgs.
"U.S. Appl. No. 12/511,527, Examiner Interview Summary mailed May 16, 2013", 3 pgs.
"U.S. Appl. No. 12/511,527, Final Office Action mailed Mar. 21, 2013", 10 pgs.
"U.S. Appl. No. 12/511,527, Non Final Office Action mailed Sep. 4, 2012", 16 pgs.
"U.S. Appl. No. 12/511,527, Response filed Nov. 30, 2012 to Non Final Office Action mailed Sep. 14, 2012", 16 pgs.
"U.S. Appl. No. 13/619,227, Notice of Allowance mailed Jul. 19, 2013", 11 pgs.
"U.S. Appl. No. 13/619,227, Response filed Apr. 1, 2013 to Restriction Requirement filed Feb. 27, 2013", 6 pgs.
"U.S. Appl. No. 13/619,227, Restriction Requirement mailed Feb. 27, 2013", 6 pgs.
"U.S. Appl. No. 13/619,269, Non Final Office Action mailed Dec. 13, 2012", 13 pgs.
"U.S. Appl. No. 13/619,269, Notice of Allowance mailed Mar. 22, 2013", 8 pgs.
"U.S. Appl. No. 13/619,269, Preliminary Amendment filed Sep. 14, 2012", 3 pgs.
"U.S. Appl. No. 13/619,269, Response filed Mar. 11, 2013 to Non Final Office Action mailed Dec. 12, 2012", 12 pgs.
"Australian Application Serial No. 2005300099, Office Action mailed Jan. 24, 2011", 2 pgs.
"Australian Application Serial No. 2005300099, Response filed Feb. 8, 2011 to Office Action mailed Jan. 24, 2011", 19 pgs.
"Canadian Application Serial No. 2,555,283, Office Action mailed Dec. 4, 2012", 6 pgs.
"Canadian Application Serial No. 2,555,283, Response filed May 27, 2013 to Office Action mailed Dec. 4, 2012", 23 pgs.
"Canadian Application Serial No. 2,555,283, Response filed Jun. 13, 2012 to Office Action mailed Mar. 21, 2012", 15 pgs.
"Canadian Application Serial No. 2,585,862, Office Action mailed Aug. 16, 2011", 3 pgs.
"Canadian Application Serial No. 2,585,862, Office Action mailed Nov. 21, 2012", 5 pgs.
"Canadian Application Serial No. 2,585,862, Response filed May 7, 2013 to Office Action mailed Nov. 21, 2012", 16 pgs.
"Canadian Application Serial No. 2,585,862, Response filed Jun. 13, 2012 to Office Action mailed Mar. 21, 2012", 7 pgs.
"European Application Serial No. 05712204.6, Office Action mailed Oct. 8, 2010", 7 pgs.
"European Application Serial No. 05712204.6, Office Action mailed Oct. 24, 2006", 2 pgs.
"European Application Serial No. 05712204.6, Response filed Jan. 14, 2011 to Office Action mailed Oct. 8, 2010", 18 pgs.
"European Application Serial No. 05712204.6, Response filed Nov. 9, 2006 to Office Action mailed Oct. 24, 2006", 1 pg.
"European Application Serial No. 05712204.6, Supplementary European Search Report mailed Dec. 18, 2008", 3 pgs.
"European Application Serial No. 05793736.9, European Search Report mailed Jan. 7, 2008", 6 pgs.
"European Application Serial No. 05793736.9, Office Action mailed Jul. 14, 2008", 1 pg.
"European Application Serial No. 05793736.9, Response filed Nov. 24, 2008 to Office Action mailed Jul. 14, 2008", 11 pgs.
"European Application Serial No. 12006956.2, Extended European Search Report mailed May 22, 2013", 8 pgs.
"European Application Serial No. 12006956.2, Invitation to Remedy Deficiencies mailed Nov. 9, 2012", 4 pgs.
"European Application Serial No. 12006956.2, Response filed Nov. 26, 2012 to Invitation to Remedy Deficiencies mailed Nov. 9, 2012", 7 pgs.
"International Application Serial No. PCT/US2005/002670, International Written Opinion mailed Jun. 28, 2006", 3 pgs.
"International Application Serial No. PCT/US2005/031127, International Written Opinion mailed Sep. 26, 2006", 3 pgs.
"International Application Serial No. PCT/US2006/022428, International Preliminary Report on Patentability mailed Dec. 11, 2007", 4 pgs.
"International Application Serial No. PCT/US2006/022428, International Search Report mailed Oct. 26, 2007", 1 pg.
"International Application Serial No. PCT/US2006/022428, Written Opinion mailed Oct. 26, 2007", 3 pgs.
"Japanese Application Serial No. 2007-538901, Office Action mailed Jan. 20, 2010", 9 pgs.
"Japanese Application Serial No. 2007-538901, Response filed Jul. 20, 2010 to Office Action mailed Jan. 20, 2010", 16 pgs.
"Knee Implant Surgery Techniques Can Obscure Tech Advances-NIH Panel", FDC Reports, The Gray Sheet, (Dec. 15, 2003), 1 pg.
"Knee Implant Wear Debris, Changing Demographics Weighed by NIH Panel", FDC Reports, The Gray Sheet, (Dec. 1, 2003), 1 pg.
"Korean Application Serial No. 10-2007-7011837, Office Action mailed Jun. 22, 2011", 4 pgs.
"Korean Application Serial No. 1020067018160, Request for Substantive Examination and Amendment filed Dec. 4, 2009", w/English claims, 29 pgs.
"NIH Consensus: More Knee Replacements Among Young, Old to Grow Market", FDC Reports, The Gray Sheet, (Dec. 15, 2003), 1 pg.
Delio, Michelle, "Hoping for a Knee-Jerk Reaction", Wired News, [Online]. Retrieved from the internet: <http://wiredvig.wired.com/news/medtech/0,1286,62716,00.html?tw-newsletter_to>, (2004), 3 pgs.
Eckhoff, D. G, et al., "Three-Dimensional Morphology and Kinematics of the Distal Part of the Femur Viewed in Virtual Reality", Journal of Bone & Joint Surgery, vol. 85-A, Supplement 4, (2003), 97-104.
Howe, Robert D, et al., "Robotics for Surgery", Annual Rev. Biomed. Eng., (1999), 211-240.
Mihalko, W. H, et al., "Comparison of Ligament-Balancing Techniques During Total Knee Arthroplasty", Journal of Bone & Joint Surgery, vol. 85-A, Supplement 4,, (2003), 132-135.
Palmer, et al., "Total Knee Arthoplasty", [Online]. Retrieved from the internet: <http://www.emedicine.com/orthoped/topic347.htm.>, (2003), 18 pgs.

(56) References Cited

OTHER PUBLICATIONS

Rapp, "Electronic Knee Implant May Benefit Future TKR Patients", Orthopedics Today, vol. 25, No. 3, (Mar. 2005), 14-15.
Ries, et al., "Soft-Tissue Balance in Revision Total Knee Arthroplasty", Jnl. Bone & Jt. Surg., vol. 86-A Supplement 1, (2003), 82-86.
Ries, M. D, et al., "Soft-Tissue Balance in Revision Total Knee Arthroplasty", Journal of Bone & Joint Surgery, vol. 85-A, Supplement 4,, (2003), 38-42.
Synvasive Technology Inc, "Achieve Dynamic Balance—Improve your demanding patient's post-op stability", 2005 Annual Meeting of Orthopedic Surgeons (Washington DC), (2005), 2 pgs.
"European Application Serial No. 12006956.2, Summons to Attend Oral Proceedings mailed May 13, 2015", 10 pgs.
"Canadian Application Serial No. 2,877,645, Office Action mailed Feb. 12, 2016", 6 pgs.
"Canadian Application Serial No. 2,877,645, Response filed Aug. 12, 2016 to Office Action mailed Feb. 12, 2016", 21 pgs.

* cited by examiner

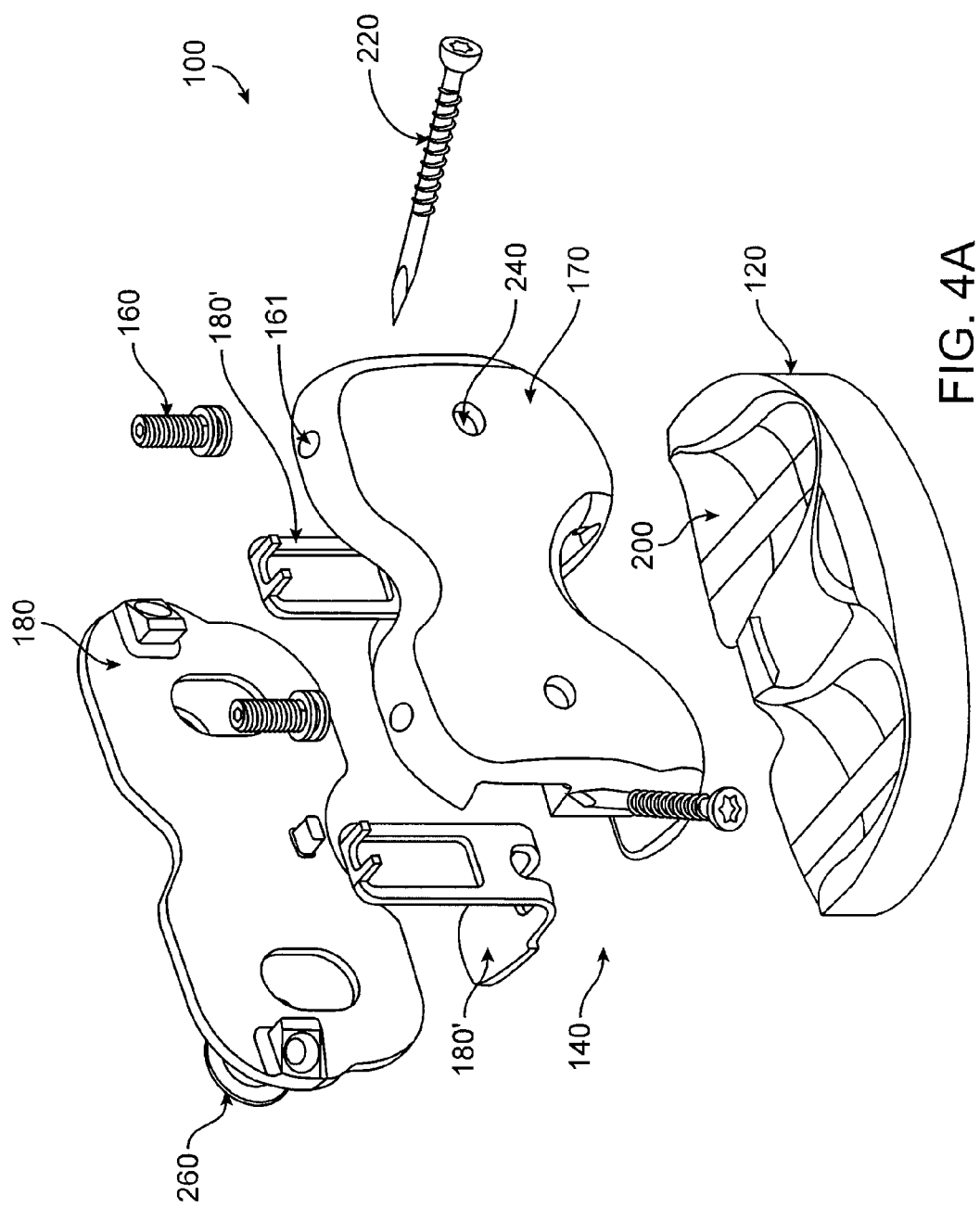

DYNAMIC KNEE BALANCER WITH FORCE OR PRESSURE SENSING

CROSS REFERENCE TO RELATED APPLICATIONS

The present patent document is a continuation of, and claims the benefit of priority to, U.S. patent application Ser. No. 12/511,527, filed on Jul. 29, 2009, which is a divisional of, and claims the benefit of priority to, U.S. patent application Ser. No. 10/973,936, filed Oct. 25, 2004, which is a continuation-in-part of, and claims the benefit of priority to, U.S. patent application Ser. No. 10/773,608, filed Feb. 6, 2004, the full disclosures of each of which are hereby incorporated by reference.

BACKGROUND OF THE INVENTION

The present invention relates generally to medical/surgical devices, systems and methods. More specifically, the invention relates to devices, systems and methods for enhancing a knee surgery procedure.

Total knee replacement surgery, also referred to as total knee arthroplasty ("TKA"), is becoming an increasingly important treatment for chronic knee pain and joint dysfunction. A recent panel of the National Institutes of Health at a Consensus Development Conference recognized that approximately 300,000 TKA surgeries are performed annually in the U.S. for end-stage knee arthritis. The NIH panel agreed that although advances have been made in TKA surgical devices and techniques, improved outcomes through further innovations should still be diligently pursued. The panel concluded that techniques for placing artificial knee prostheses, in particular, should be improved to provide better outcomes and reduce wear of the prostheses, to thus reduce the need for repeat TKA surgeries. If advances in TKA continue to be made, the procedure may become more readily available to younger patients, obese patients, and the like, who may need TKA but who do not fall within in the "ideal" age range traditionally defined as between 60 and 75 years old. Improved techniques and devices would also mean enhanced outcomes for all TKA patients, with better functioning of the knee joint and longer useful life of the prosthetic knee.

The knee is generally defined as the point of articulation of the femur with the tibia. Structures that make up the knee include the distal femur, the proximal tibia, the patella, and the soft tissues within and surrounding the knee joint. Four ligaments are especially important in the functioning of the knee—the anterior cruciate ligament, the posterior cruciate ligament, the medial collateral ligament, and the lateral collateral ligament. In an arthritic knee, protective cartilage at the point of articulation of the femur with the tibia has been worn away to allow the femur to directly contact the tibia. This bone-on-bone contact causes significant pain and discomfort. The primary goals of a TKA procedure are to replace the distal end of the femur, the proximal end of the tibia, and often the inner surface of the patella with prosthetic parts to avoid bone-on-bone contact and provide smooth, well-aligned surfaces for joint movement, while also creating a stable knee joint that moves through a wide range of motion.

One of the greatest challenges in TKA surgery is to properly balance ligament tension, especially in the medial and lateral collateral ligaments, through a full range of motion of the knee. The collateral ligaments, which connect the distal femur and proximal tibia on the medial and lateral aspects of the knee, account for much of the stability and movement of the knee. If one of the collateral ligaments is too lax or too tight relative to the other collateral ligament, the knee will typically be unstable, range of motion may be limited, the patella may track improperly, and the femur and/or tibia may wear unevenly, leading to arthritis and pain. Uneven ligament tension after TKA surgery will typically cause joint instability and poor patellar tracking, limited range of motion, and impaired function of the knee, as well as uneven, increased wear of the prosthetic device, which often necessitates repeat surgery. Thus, it is imperative for the short- and long-term success of a TKA procedure to achieve balanced ligament tension in the knee through a full range of motion.

Balancing ligament tension during TKA surgery is complicated by the fact that the natural knee does not operate like a hinge moving about a single axis. The knee exhibits dynamic external rotation of the tibia relative to the femur as the knee moves from its flexed to its fully extended position. This automatic rotation of the tibia occurs in the opposite direction when the knee is flexed from its fully extended position to produce an internal rotation of the tibia relative to the femur. Thus, the natural knee exhibits a rotary laxity that allows the tibia to rotate through a limited internal and external arc, during knee flexion. Additionally, the femur translates anteriorly and posteriorly as the tibia is being flexed about it, bringing yet another movement variable into the equation. Thus, the ligaments of the knee, along with the femur, tibia and patella, create a truly dynamic bio-mechanism, making ligament tension balancing in TKA surgery extremely challenging. Many articles and studies have been devoted to ligament tension balancing in TKA, such as the following: Mihalko, W H et al., "Comparison of Ligament-Balancing Techniques During Total Knee Arthroplasty," Jnl. Bone & Jt. Surg., Vol. 85-A Supplement 4, 2003, 132-135; Eckhoff, D G et al., "Three-Dimensional Morphology and Kinematics of the Distal Part of the Femur Viewed in Virtual Reality, Jnl. Bone & Jt. Surg., Vol. 85-A Supplement 4, 2003, 97-104; and Ries, M D, et al., "Soft-Tissue Balance in Revision Total Knee Arthroplasty," Jnl. Bone & Jt. Surg., Vol. 85-A Supplement 4, 2003, 38-42.

One technique for balancing collateral ligament tension during a TKA procedure involves cutting fibers of one or both ligaments to decrease ligament tension—a technique referred to as "ligament release." Although ligament release is still commonly used, the disadvantage of this technique is that it requires actually cutting ligament tissue, thus weakening the ligament(s) and leaving less room for error if future releases or TKA procedures are required.

Rather than or in addition to ligament release, the components of a total knee prosthesis may be selected and positioned to balance ligament tension. Since the femoral and tibial components of the prosthesis are attached to cut surfaces of the distal femur and proximal tibia respectively, placement and orientation of the bone cuts are also critically important. Typically, the tibial component of the prosthesis is positioned on a flat, horizontal cut surface of the proximal tibia (at a 90 degree angle relative to the long axis of the tibia), and the position and orientation of the tibial component typically do not vary greatly from knee to knee. Therefore, most of the variation in positioning of the total knee prosthesis typically occurs in positioning the femoral component and the femoral bone cuts. The surgeon attempts to make these femoral bone cuts to achieve a position and orientation of the femoral prosthetic component so as to optimally balance ligament tension through a full range of motion of the knee. As with ligament release however, it is often very challenging to position the femoral bone cuts and femoral prosthetic component to provide ideal ligament tension through the range of motion. This is due primarily to the complexity of motion about the knee, as described above, and the difficulty of placing the femoral component so as to maintain desired ligament tension through the full range of motion. Specifically, the rotational, proximal/distal and anterior/posterior orientations and locations of the femoral component are all critical for duplicating the kinematics of the knee.

In a typical TKA procedure, multiple cuts are made to the distal femur before attaching the femoral component of the prosthesis. Most procedures, for example, involve making a distal cut across the distal end of the femur, anterior and posterior cuts, and angled anterior and posterior chamfer cuts to help secure the femoral component solidly in place. In order to effectively and accurately make these resections, orthopedic surgeons typically use a cutting block or cutting guide, used to guide a surgical saw blade or rotary tool, which is temporarily attached to the distal end of the femur. Positioning of such a cutting block, therefore, is crucial to forming well-positioned bone cuts for attachment of the femoral prosthetic component.

A number of devices and techniques have been described that attempt to facilitate ligament balancing during a TKA procedure. Some techniques, such as those described in U.S. Pat. No. 5,733,292, involve trial prosthesis components which are used after femoral and tibial bone cuts are made to assess ligament tension. Some devices, such as those described in U.S. Patent Application Publication No. 2003/0187452, are used to measure a gap between the distal femur and proximal tibia in extension and to help a surgeon recreate that same gap when the knee is in flexion. Other "gap checking" devices are described in U.S. Pat. No. 6,575,980. Other devices have been developed to help measure an amount of ligament tension or to apply a desired amount of tension to the ligaments. U.S. Pat. No. 4,501,266, for example, describes a knee distraction device for applying a desired amount of tension. Many paddle-like devices have been suggested for applying or measuring tension across a knee joint, such as the devices described in U.S. Pat. Nos. 5,597,379; 5,540,696; 5,800,438; 5,860,980; 5,911,723; and 6,022,377.

One proposed alternative to the cutting block technique for making bone cuts on a distal femur involves the use of robotic surgical systems for making distal femoral bone cuts. With robotic surgery and surgical navigation, a surgical saw blade or bur is still used, but the bone cuts are positioned as a result of fiducial-based or shape-based registration of the patient's anatomy. In fiducial-based approaches, fiducials, or markers are attached to pertinent anatomical structures prior to imaging. During surgery, the markers are exposed, and a sensor system conveys their location to the computer. A wide variety of sensing systems available, including optical trackers, electromagnetic transceivers, articulated probe arms, and ultrasonic and laser range finders. In shape-based approaches, the shapes of anatomical structures are fitted to preoperative image data. The patient measurements can be obtained from a variety of sensing techniques, including tracing curves, scanning distances, or processing images, via one or some of the aforementioned sensing systems. One description of the use of robotic surgery systems in knee surgery procedures is found in Howe, R D, and Matsuoka, Y, "Robotics for Surgery," Annu. Rev. Biomed. Eng. 1999, 01:211-240.

Although some of the devices and techniques described above have helped enhance and facilitate TKA procedures, currently available devices and techniques still have a number of shortcomings. Most importantly, currently available devices do not allow a physician to adjust ligament tension in a knee and also receive positional information based on that adjustment that can be used to facilitate completion of the TKA surgery. For example, many currently available devices are applied only in extension or only in flexion of the knee, or must be removed and replaced when the knee is moved from extension to flexion. Thus, it is difficult or impossible to assess ligament tension through the full range of motion using many currently available devices. Some devices rely on measuring a gap or amount of tension in extension and then recreating the gap or tension in flexion. Again, this does not always result in collateral ligament balance throughout the range of motion. Still other devices are very cumbersome and/or complex. Many include large parts which fit external to the knee joint and necessitate the patella being moved to the side during measurement or other phases of the TKA procedure. Furthermore, current devices typically do not reside primarily within the joint space during a surgical procedure to allow for the natural movements, rotations and translations of the tibia and femur as the knee is flexed through a range of motion. In some techniques, bone cuts are made before ligament balancing is achieved, thus often requiring re-cutting of those same bone cuts. More bone cuts mean more trauma to the patient, a longer recovery period, and less bone to work with if a second TKA is required later in life.

Although robotic surgery may provide a level of improvement over more traditional techniques, it is typically difficult or impossible using current robotic techniques to dynamically mark or register and sense the proper dynamic position to make well-positioned, subsequent bone cuts for attachment of the femoral prosthetic component. Thus, even with robotic systems, it is still challenging to achieve a desired ligament balance to enhance knee stability, range of motion and patellar tracking. These and other shortcomings of currently available devices and methods continue to make ligament balancing, and specifically collateral ligament balancing, one of the most challenging aspects of TKA surgery.

Therefore, a need exists for improved devices, systems and methods for enhancing TKA surgery and specifically for dynamically balancing ligaments during TKA to improve range of motion, stability, and patellar tracking of the prosthetic knee joint. Ideally, such devices would help a surgeon balance ligaments dynamically, through a full range of motion of the knee, allowing for the natural rotation of the tibia and the natural translation of the femur while the tibia is being flexed about it. Also ideally, such devices and methods would allow a surgeon to achieve a desired ligament tension balance before committing to and making final bone cuts to the femur. Such devices would ideally be simple to use in conjunction with cutting guides, saw blades or burs, and robotic and navigational systems, preferably allowing the patella to remain in place during assessment of ligament tension. At least some of these objectives will be met by the present invention.

BRIEF SUMMARY OF THE INVENTION

The present invention provides devices, systems and methods for enhancing knee surgery procedures, and more specifically total knee replacement procedures (total knee arthroplasty, "TKA"). Various embodiments generally include a femoral portion, a tibial portion and one or more sensors for sensing pressure exerted by the femoral and tibial portions against one another. The femoral portion is adjustable, to allow a user to adjust tension in soft tissues adjacent the knee, thus causing changes in the sensed pressure. The adjustable femoral portion also helps a user determine positioning of at least part of a knee prosthesis.

Typically, the adjustable femoral portion is separately adjustable on opposite lateral sides to adjust tension in soft tissues on either or both sides of the knee, such as the lateral and/or medial collateral ligaments. When the adjustable femoral portion is adjusted to adjust ligament tension, one or more positioning features of the femoral portion provide positioning information to help position and/or orient a cutting guide, surgical saw blade, bur, mill, surgical navigation system, robotic surgical system or the like. This positioning information is then typically used to make subsequent bone cuts to the distal femur, or to otherwise mill or shape the distal femur, so that when a femoral prosthetic component is applied, the knee has a desired stability, range of motion and/or patellar tracking. The sensor (or multiple sensors) of the device helps a user balance pressure between the femoral and tibial members while the knee is in flexion with pressure while the knee is in extension. If pressure(s) in extension to not match those in flexion, the user may choose to adjust the femoral member, thus adjusting soft tissue tension and also pressure between the femoral and tibial portions of the device. Thus, devices and methods of the invention help a user dynamically balance ligament tension in a knee during TKA surgery, without requiring ligament releases, to provide for a dynamically balanced knee after the surgery is complete.

For purposes of the present description, the terms "ligaments of the knee," "ligaments in the knee," "ligaments adjacent the knee," and the like are all synonymous and all refer generally to any ligaments within the knee joint space, around the knee, adjacent the knee, or near the knee. These terms typically refer to the ligaments that assist in the functioning of the knee, and often the ligaments referred to are the medial collateral ligament, the lateral collateral ligament, the anterior cruciate ligament and the posterior cruciate ligament. "Soft tissues adjacent the knee" or "soft tissues of the knee" include the ligaments described above as well as muscles, tendons and other soft tissues adjacent and/or in the knee. Although the following description focuses on the use of various devices and methods in TKA surgical procedures, some embodiments may suitably be used to facilitate other knee surgery procedures and/or other orthopedic joint surgery procedures.

That being said, in one aspect of the present invention, a device for performing a surgical procedure on a knee includes an adjustable femoral portion, a tibial portion and at least one sensor coupled with at least one of the femoral and tibial portions to sense pressure exerted by the femoral and tibial portions against one another. The femoral portion is adapted for removably coupling with a distal end of a femur to adjust tension in soft tissue adjacent the knee and has at least one positioning feature adapted to move relative to the distal end of the femur as the femoral portion is adjusted, thus helping position a femoral prosthetic on the distal end of the femur. The tibial portion is adapted for removably coupling with a proximal end of a tibia and movably coupling with the femoral portion to allow the knee to be moved through a range of motion without removing the femoral and tibial portions from the knee. Typically, the pressure exerted by the femoral and tibial portions against one another is caused, at least in part, by soft tissues adjacent the knee. In some embodiments, the pressure may be increased or decreased on one or both lateral sides of the knee by adjusting the femoral portion of the device.

The sensor(s) may be coupled with the tibial portion, the femoral portion or both, in various embodiments. In a preferred embodiment, sensors are coupled with only one of the two portions, to simplify the device design and function, but other embodiments may include sensors on both portions. The sensors may have any suitable shape, size and configuration. One embodiment includes a single sensor comprising a layer of pressure sensing material disposed along a surface of the femoral portion or the tibial portion to contact the distal femur or proximal tibia. In other embodiments, multiple sensors are used. Optionally, the device may further include a sensor housing plate coupled with the femoral or tibial portion and adapted to house one or more sensors. Such a sensor housing plate may be either permanently or removably coupled with the femoral portion or the tibial portion. Optionally, a connector plate may also be included for coupling the sensor housing plate with the femoral portion or the tibial portion. In some embodiments, the sensor housing plate is adapted to contact the femur or tibia, thus residing between the bone and the rest of the femoral or tibial portion. In other embodiments, the plate may be disposed out of contact with the bone.

Any suitable pressure- or force-sensing material or combination of materials may be used to form the sensor(s), and the sensors themselves may have any of a number of configurations, shapes and size. Some examples of sensors that may be used include, but are not limited to piezoelectric sensors, force sensing resistors, strain gauges, load cells, other pressure sensors and other force sensors. In some embodiments, the device further includes a processor coupled with the sensor(s) for processing sensed pressure data into usable data for providing to a user. Typically, though not necessarily, such an embodiment will also include a visual display coupled with the processor for displaying the usable data. In one embodiment, for example, the visual display comprises a digital display for providing at least one of alpha and numerical data to the user, with the device further comprising an analog to digital converter. In some embodiments, the visual display separately displays usable data representing pressure on a lateral side and a medial side of the knee.

Typically, the knee surgery device will also include one or more connectors for connecting the sensor(s) with the visual display and/or the processor. Connectors such as electrical cable, wireless infrared, electromagnetic and optical connectors may be used, as well as any other suitable connectors. In some embodiments, the visual display is directly attached to the femoral portion or the tibial portion, thus necessitating relatively short connector(s). In alternative embodiments, the visual display is removably couplable with a leg of a patient below the knee or above the knee, thus employing longer connector(s). In some embodiments, the device further includes one or more pressure selection members coupled with the sensor(s) and the femoral portion. The pressure selection member(s) are adapted to allow a user to select a desired amount of pressure exerted between the femoral and tibial portions and to automatically adjust the femoral portion to achieve the selected amount of pressure. In some embodiments, the pressure selection member(s) are adapted to allow the user to separately select desired pressures exerted between the femoral and tibial portions at medial and lateral sides of the knee.

In one embodiment of the device, the femoral portion includes a stationary femoral member for removably attaching in a fixed position to the distal end of the femur and a mobile femoral member movably coupled with the stationary femoral member to adjust the tension in the soft tissue adjacent the knee. In some embodiments, the mobile femoral member is separately adjustable on laterally opposite sides of the femoral portion. In such embodiments, adjusting on one lateral side relative to the opposite side may cause the mobile femoral member to rotate relative to the distal femur. The positioning feature(s) of the adjustable femoral member may include, but are not limited to, apertures, drill bit guides, surface markers, surface features, measurement devices, embedded markers, fiducials, transponders, transceivers and/or sensors. In various embodiments, the positioning feature(s) may serve a number of different functions for a user, such as facilitating placing a cutting guide on the distal femur for making bone cuts, making one or more bone cuts on the distal femur, or positioning a prosthetic femoral component on the distal femur.

In some embodiments, the tibial portion comprises at least one shim, paddle, plate, bar, platform or rod. In one embodiment, the tibial portion comprises a plurality of tibial shims having different thicknesses or heights, and any one of the plurality of shims may be selected for engaging with the proximal end of the tibia to provide a desired amount of tension in soft tissue adjacent the knee. In some embodiments, the femoral and tibial portions are movably coupled via force provided by the soft tissue adjacent the knee. Also in some embodiments, the femoral and tibial portions may be adapted to reside primarily within a joint space between the distal end of the femur and the proximal end of the tibia. In some embodiments, the patella of the knee remains approximately in its anatomical position while the femoral and tibial portions are engaged and the knee is moved through the range of motion.

In another aspect of the invention, a device for performing a surgical procedure on a knee includes a femoral portion for removably coupling with a distal end of a femur, a tibial portion for removably coupling with a proximal end of a tibia and movably coupling with the femoral portion to allow the knee to be moved through a range of motion without removing the femoral and tibial portions from the knee, means for adjusting the position of the femoral portion relative to the tibial portion to adjust tension in soft tissue adjacent the knee, and at least one sensor coupled with at least one of the femoral and tibial portions to sense pressure exerted by the femoral and tibial portions against one another.

In yet another aspect of the present invention, a system for performing a surgical procedure on a knee includes a knee adjustment device including an adjustable femoral portion and a tibial portion, and a sensor device coupled with the femoral or tibial portion. The adjustment device may include any of the features described above. The sensor device includes at least one sensor coupled with the femoral or tibial portion to sense pressure exerted by the femoral and tibial portions against one another, a processor coupled with the sensor(s) for processing sensed pressure data into usable data for providing to a user, and a visual display coupled with the processor for displaying the usable data. The sensor(s), processor and visual display may include any features and combinations described above.

In another aspect of the present invention, a method for sensing pressure in a knee during a surgical procedure on the knee involves engaging femoral and tibial portions of a knee adjustment device with the knee, sensing pressure exerted by the femoral and tibial portions against one another, using at least one sensor coupled with the femoral or tibial portion, displaying data describing the sensed pressure, and moving the knee through a range of motion while the knee adjustment device remains engaged with the knee. Optionally, the method may further involve adjusting the femoral portion of the knee adjustment device to adjust tension in soft tissue adjacent the knee. Adjusting the tension affects the pressure exerted by the femoral and tibial portions against one another. In various embodiments, the adjusting step may be performed before the moving step, after the moving step, or both. In some embodiments, the adjusting step is performed one or more times to balance pressure data displayed while the knee is flexed with pressure data displayed while the knee is extended. In an alternative embodiment, tension/pressure adjustment is achieved by inserting and removing multiple differently-sized tibial portions. Again, this may be performed before moving the knee, after moving the knee, or both. In one embodiment, various tibial portions are used to balance pressure when the knee is flexed with pressure when the knee is extended. In some embodiments, adjustments may be made to both the femoral and tibial members.

Typically, though not necessarily, the method also involves processing the sensed pressure into the data describing the pressure. In some embodiments, for example, processing the data involves converting analog data to digital data. Pressure sensing may be achieved in a number of different ways. In one embodiment, for example, sensing the pressure involves transmitting a voltage to at least one sensor, measuring the voltage after it has passed through the sensor(s), determining a percentage of the voltage passed through the sensor(s) relative to the voltage transmitted to the sensors, and deriving the pressure from the percentage. In other embodiments, sensing may involve using one or more sensors such as but not limited to piezoelectric sensors, force sensing resistors, strain gauges, load cells, other pressure sensors or other force sensors.

In one embodiment, displaying the data involves displaying at least a first number representing the pressure in a medial portion of the adjustment device and displaying at least a second number representing pressure in a lateral portion of the adjustment device. Optionally, the method may further involve receiving an input from a user of a desired amount of pressure to be exerted by the femoral and tibial members against one another and automatically adjusting the femoral portion of the adjustment device to achieve the desired amount of pressure. In some embodiments, receiving the input includes receiving a first amount of desired pressure for a medial side of the knee and a second amount of desired pressure for a lateral side of the knee. Some embodiments optionally include automatically adjusting the adjustment device to balance the pressure exerted by the femoral and tibial members against one another while the knee is flexed and extended.

Further details of these and other embodiments are described more fully below, with reference to the attached drawing figures.

BRIEF DESCRIPTION OF THE DRAWINGS

FIG. 4A is a front-perspective, exploded view of a knee balancing device according to one embodiment of the present invention.

DETAILED DESCRIPTION OF THE INVENTION

As discussed above, the present invention provides devices, systems and methods primarily intended for enhancing total knee arthroplasty (TKA) surgical procedures. Although these devices, systems and methods are used primarily in TKA, however, some embodiments may be used to enhance other knee surgery procedures or surgical procedures on other joints, such as an elbow joint.

That being said, devices, systems and methods of the invention generally help a surgeon to balance ligament tension in a knee during a TKA procedure and thereby help the surgeon perform the TKA so as to achieve a desired ligament balance when the surgery is complete. Devices, systems and methods of the invention generally facilitate dynamic balancing of ligaments of the knee, such that these ligaments remain balanced through a range of motion about the knee. Oftentimes, such dynamic balancing helps create a prosthetic knee that has a desirable level of stability, patellar tracking and range of motion.

Figure 1A:
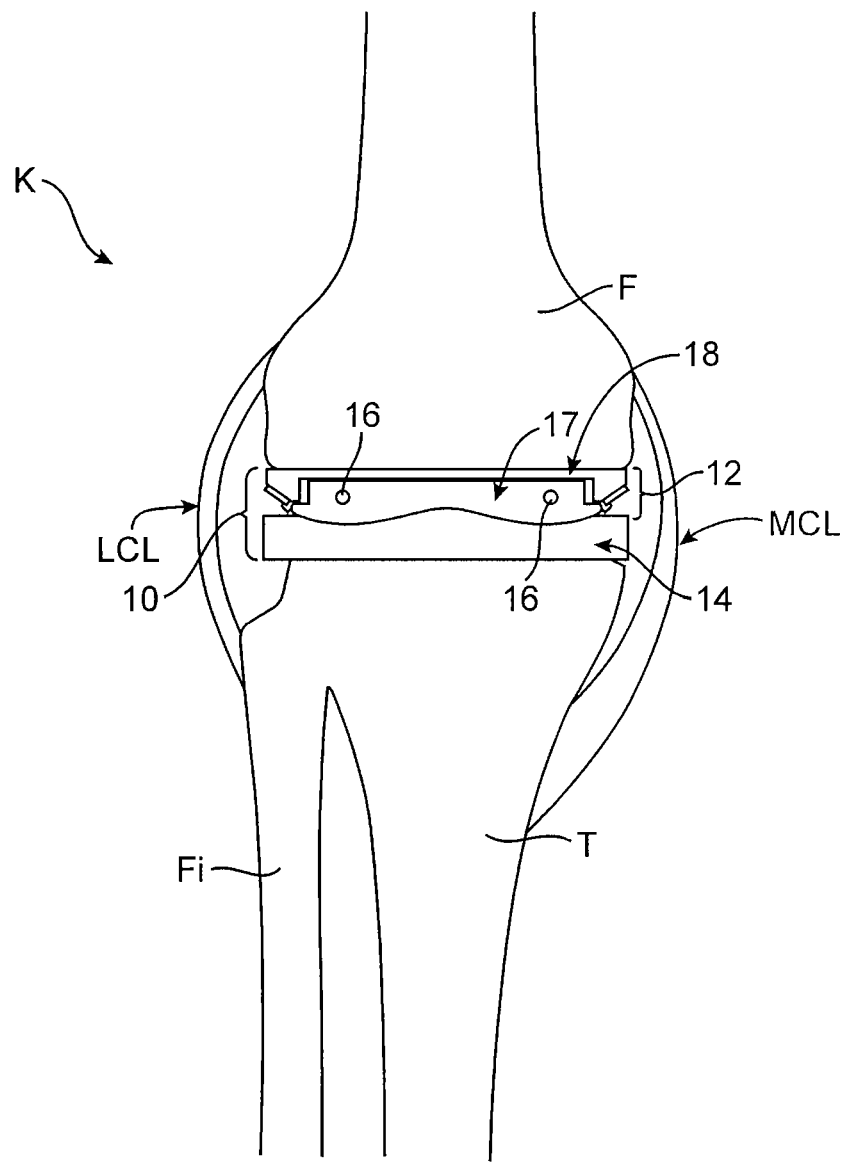
FIG. 1A is a frontal view of a knee in extension, with a knee balancing device according to one embodiment of the invention in place within the knee joint.

With reference now to FIG. 1A, a frontal view of a right knee K is shown in extension, with a knee balancing system 10 in place within the knee joint space. The anatomical components of the knee K that are pertinent to this description include a distal femur F, a proximal tibia T, a medial collateral ligament MCL, and a lateral collateral ligament LCL. (Also labeled is the proximal fibula Fi, to which the LCL attaches.) The knee K is shown without a patella, medial collateral ligament or lateral collateral ligament, for clarity, but many embodiments may be used while the patella is in its anatomical position on the anterior aspect of the knee K. In FIG. 1A, a portion of the distal end of the distal femur F and a portion of the proximal end of the proximal tibia T have been cut or shaved off, to create level surfaces on which to place femoral member 12 and a tibial member 14, respectively, of dynamic knee balancing system 10. In various embodiments, a knee balancing device may be provided as only a femoral member, for example to be used with off-the-shelf tibial trial inserts. In other embodiments, knee balancing system 10, comprising femoral member 12 and tibial member 14 may be provided.

In the embodiment shown, femoral member 12 is adjustable to adjust tension in the MCL, the LCL, or both. Adjustability may be achieved by any suitable means, some of which are described in more detail above and below. In one embodiment, for example, one or more adjustment members 16, which may comprise screws, pins, levers, spring-loaded mechanisms, shape memory materials or the like, are coupled with femoral member 12 to provide adjustability. In some embodiments, adjustment members 16 may be used for separately adjusting femoral member 12 on either side to separately adjust tension in the MCL or the LCL.

In general, femoral member 12, tibial member 14 and any of their component parts may be manufactured from any suitable material now known or hereafter discovered. For example, femoral member 12 and/or tibial member 14 in some embodiments may be manufactured from one or more plastics, composites and/or metals, such as aluminum, stainless steel, composite, cobalt-chrome, titanium, or the like. These or any other suitable material(s) and combinations of materials may be used in various embodiments.

As shown in FIG. 1A and subsequent figures, knee balancing system 10 is typically disposed primarily within the joint space of knee K during a TKA surgery, thus providing for more convenient manipulation of the knee, anatomical positioning of the patella during surgery and the like. In alternative embodiments, however, a knee balancing device or system could be engaged with the knee at a location external to the knee joint. For example, in one embodiment the device may comprise an externally applied frame that performs the same functions as the devices described herein. In such embodiments, some or all of the knee balancing device may be located external to the knee joint, thus not fitting within the knee joint space during the surgical procedure.

Figure 1B:
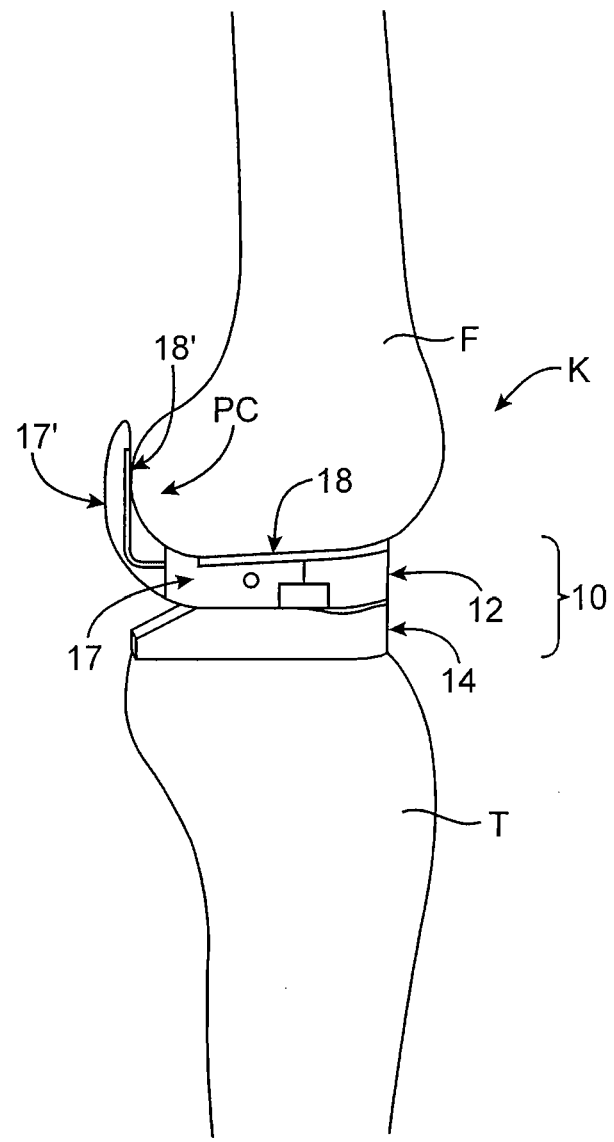
FIG. 1B is a side view of the knee in extension and knee balancing device shown in FIG. 1A.

Referring now to FIG. 1B, the knee K is shown from a side view. In this and subsequent figures, the collateral ligaments MCL and LCL, other ligaments such as the posterior cruciate ligament PCL, and the fibula Fi are removed for clarity. As is visible in this view, femoral member 12 suitably comprises a stationary femoral member 18 and an adjustable femoral member 17. Stationary femoral member 18 is typically removably attached to a surface of the distal femur F, often a cut surface at the distal end of the distal femur F, and adjustable femoral member 17 is coupled with stationary femoral member 18. Stationary femoral member 16 includes at least one stationary posterior condylar member 18' extending posteriorly to contact at least one of the medial and lateral posterior condyles PC of the distal femur F. Typically, stationary femoral member 18 includes two stationary posterior condylar members 18', one for each posterior condyle PC. Similarly, adjustable femoral member 17 suitably includes one or more (preferably two) adjustable posterior condylar members 17' extending posteriorly emulate the two posterior condyles PC. As is described more fully below, posterior condylar members 17', 18' allow femoral member 12 to be adjusted to balance ligament tension in the knee K and also allow knee balancing system 10 to remain in place within the joint space while the knee K is moved through a range of motion. In various embodiments, stationary femoral member 18 and stationary posterior condylar members 18' may be either multiple, couple parts or may be one piece or extrusion. Similarly, adjustable femoral member 17 and adjustable posterior condylar members 17' are all one piece or extrusion in some embodiments, but may alternative comprise multiple coupled parts.

Typically, adjustable femoral member 17 is movably engageable with tibial member 14 to allow knee balancing system 10 to remain in place within the knee joint space while the knee K is moved through a range of motion. In some embodiments, such as the one shown in FIG. 1 and subsequent figures, adjustable femoral member 17 and tibial member 14 are movably engaged with one another via force applied by the ligaments of the knee K, especially the MCL and LCL. In other words, femoral member 12 and tibial member 14 are two separate components which are brought together into a movable/slidable coupling by ligament force. Such coupling of adjustable femoral member 17 and tibial member 14 via ligament force provides for dynamic balancing of the knee through a full range of motion. In various alternative embodiments, ligament force may not be used for coupling femoral member 12 with tibial member 14, and instead a passive mechanical coupling may be used.

Figure 1C:
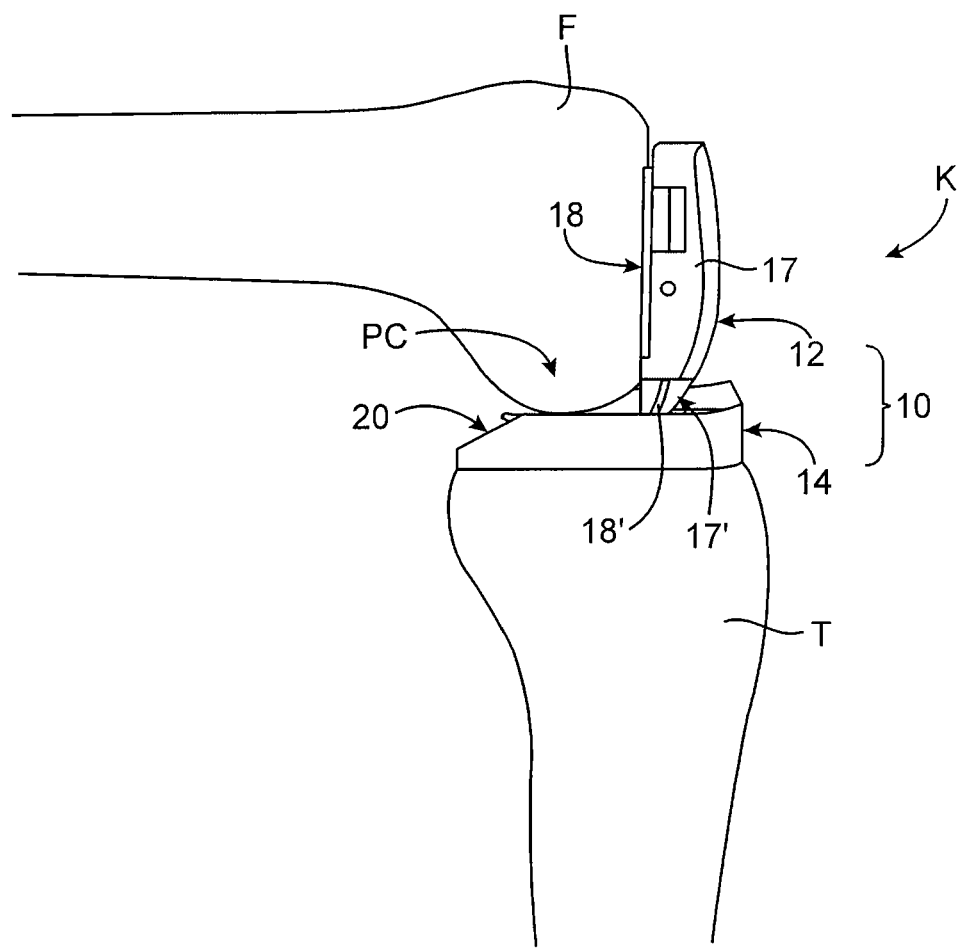
FIG. 1C is a side view of the knee and knee balancing device shown in FIGS. 1A and 1B, with the knee in a position of flexion.

With reference now to FIG. 1C, knee balancing system 10 is shown with the knee K in flexion. It can be seen here that stationary posterior condylar member 18' and adjustable posterior condylar member 17' are slidably engageable with complementary grooves 20 on tibial member 14. Thus, knee balancing system 10 is movable/slidable through approximately a full range of motion of the knee K, from full extension to full flexion and vice versa.

Figure 1D:
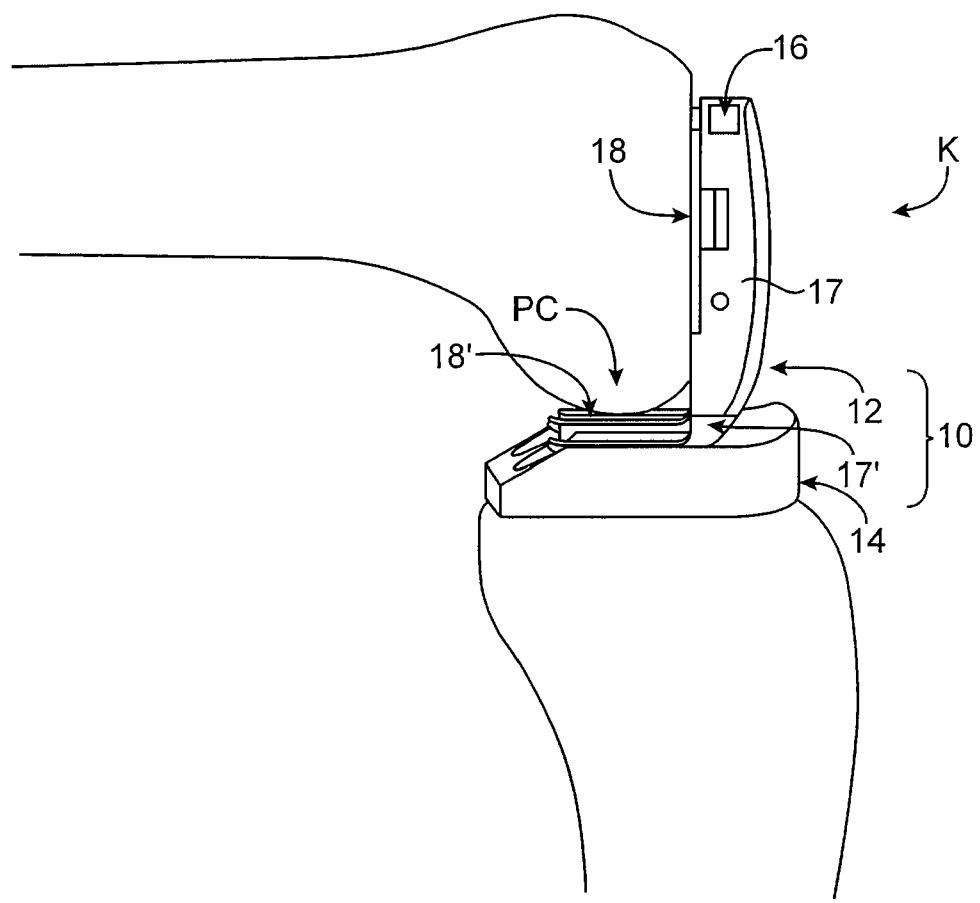
FIG. 1D is a side view of the knee and knee balancing device shown in FIGS. 1A-1C, with the knee balancing device adjusted to achieve a desired ligament tension balance according to one embodiment of the invention.

Referring to FIG. 1D, knee balancing system 10 is shown after an adjustment has been made to adjustable femoral member 17. In one embodiment, adjustable femoral member 17 is separately adjustable on either side to separately adjust tension in the MCL and/or the LCL. Such adjustment(s) may be achieved by any suitable means, such as manual adjustment via a screw or other adjustment member, self-adjustment via a spring-loaded mechanism, or the like. In the embodiment shown, adjustment member 16 is adjusted to move adjustable femoral member 17 relative to stationary femoral member 18. As adjustment member 16 is adjusted, adjustable femoral member 17 rotates relative to stationary femoral member 18, thus causing adjustable posterior condylar member 17' to move away from stationary posterior condylar member 18'. This movement creates a larger joint space on the side of adjustment, thus tightening the collateral ligament on that side. Meanwhile, the distal femoral portion of adjustable femoral member 17 has rotated relative to the distal femoral portion of stationary femoral member 18, approximately about the long axis of the femur F. If adjustment members 16 on both sides of adjustable femoral member 17 are adjusted in the same direction, adjustable femoral member 17 may be caused to move anteriorly or posteriorly relative to stationary femoral member 18. Thus, adjustable femoral member 17 may be adjusted rotationally as well as in an anterior/posterior orientation.

Figure 1E:
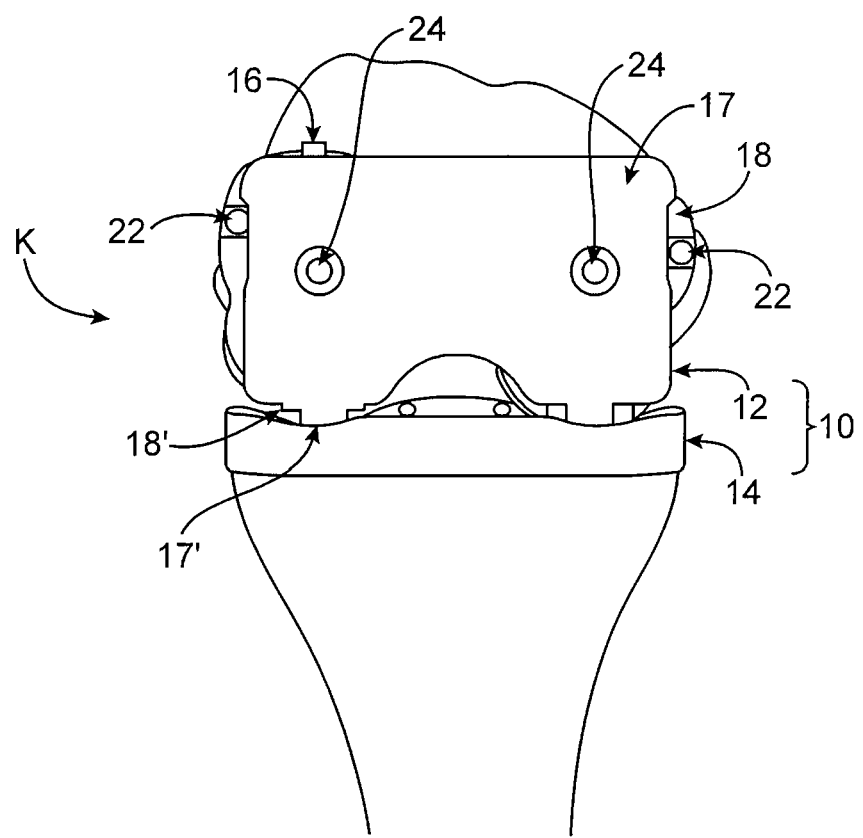
FIG. 1E is a frontal view of the knee and knee balancing device shown in FIGS. 1A-1D, with the knee balancing device adjusted to achieve a desired ligament tension balance according to one embodiment of the invention.

With reference now to FIG. 1E, the knee K and knee balancing system 10 of FIG. 1D is shown in frontal view. Here it can be seen that adjustment of adjustment member 16, on the lateral side of the distal femur F, has caused adjustable posterior condylar member 17' on the lateral side to move away from stationary posterior condylar member 18' on the lateral side, thus increasing the height of the joint space on the lateral side and rotating adjustable femoral member 17 slightly, relative to the distal femur. Adjustable femoral member 17 includes at least one positioning feature for providing positional information for facilitation the TKA procedure. As described above, the positioning feature(s) may include any of a number of different features, such as apertures, surface markers, embedded markers, fiducials, transmitters, transponders, transceivers, sensors and/or the like. These positioning features provide positional information that can then be used to facilitate the TKA procedure. For example, apertures may act as drill bit guides for drilling holes to apply a cutting guide to the femur F to make subsequent bone cuts. In another embodiment, apertures may contain fiducials or markers to provide information to a navigational system and/or robotic surgical system for positioning subsequent bone cuts or otherwise shaping the distal femur F via milling, burring or the like. Various embodiments have been fully described above, and any suitable positioning features and positional information may be used in various embodiments.

In the embodiment shown, adjustable femoral member 17 includes two apertures 24 as positioning features. Apertures 24 extend through adjustable femoral member 17 and also through stationary femoral member 18 such that apertures 24 may be used to guide a drill bit to form holes in the distal femur F. Of course, as just discussed, apertures 24 can serve any of a number of other functions, such as carrying fiducials, sensors, markers or the like. In some embodiments, corresponding apertures in stationary femoral member 18 are large enough to allow for movement of apertures 24 on adjustable femoral member 17 such that apertures 24 extend all the way to the cut surface of the distal femur F. When apertures 24 are used to drill holes for a cutting guide, the balancing system 10 is removed, holes are used to attach a cutting guide to the distal femur F, and the cutting guide used to make subsequent bone cuts on the femur F. Once these bone cuts are made, a femoral prosthetic component is typically placed on the cut distal end of the femur. These final bone cuts thus determine the position and orientation of the femoral prosthetic component. Alternatively, positioning information may be used to orient/position bone cuts by some other means (not using a cutting guide), such by guiding a saw blade, rotary cutter, bur or the like to make the actual bone cuts. In some embodiments, position information may be used to guide a robotic surgical system, to enhance the procedure via a navigational system, or the like.

Also shown in FIG. 1E are two stationary femoral member attachment screws 22. These screws are used to removably attach stationary femoral member 18 to the distal femur F. Any other suitable attachment device(s) may be used instead of or in addition to attachment screws 22 to attach stationary femoral member 18 to the distal femur F. For example, adhesives, pins and/or the like may be used in some embodiments.

Figure 2B:
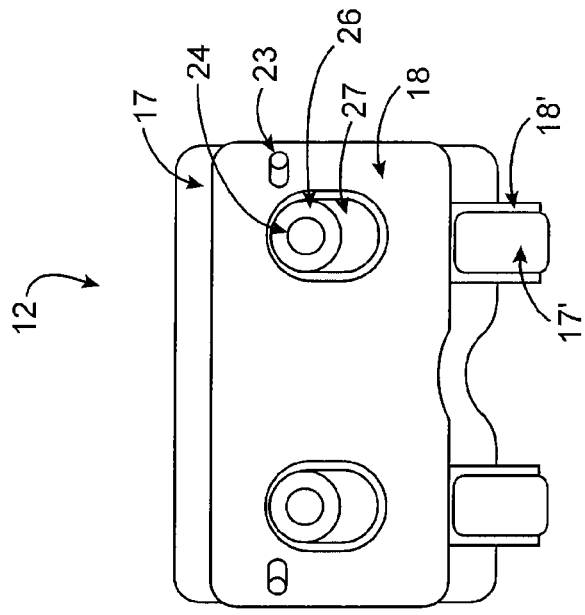
FIG. 2B is a rear view of the knee balancing device shown in FIG. 2A.
Figure 2C:
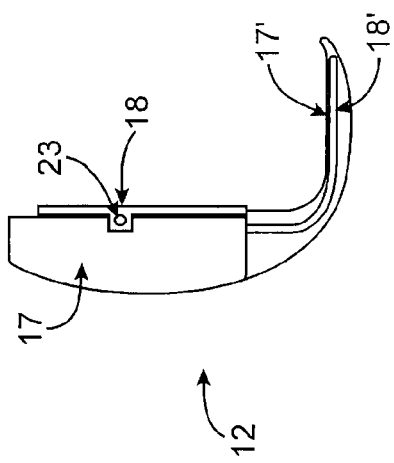
FIG. 2C is a side view of the knee balancing device shown in FIGS. 2A and 2B.
Figure 2A:
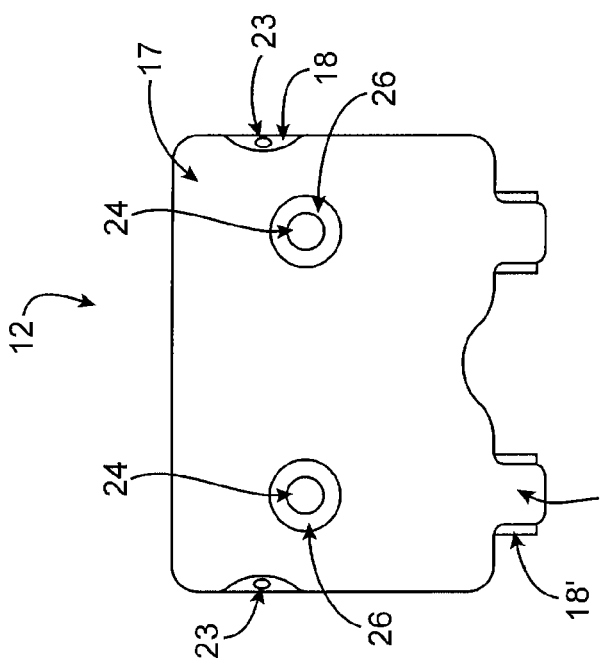
FIG. 2A is a frontal view of a knee balancing device according to one embodiment of the present invention.

FIGS. 2A-2C are anterior, posterior and side views, respectively, of an embodiment of femoral member 12. These figures show two screw holes 23 used for attaching stationary femoral member 18 to a distal femur. They also show drill guide apertures 24 which are formed by bushings 26 coupled with adjustable femoral member 17 and stationary femoral member 18. Bushings 26 move along slots 27 in stationary femoral member 17 as femoral member 12 is adjusted.

Figure 3A:
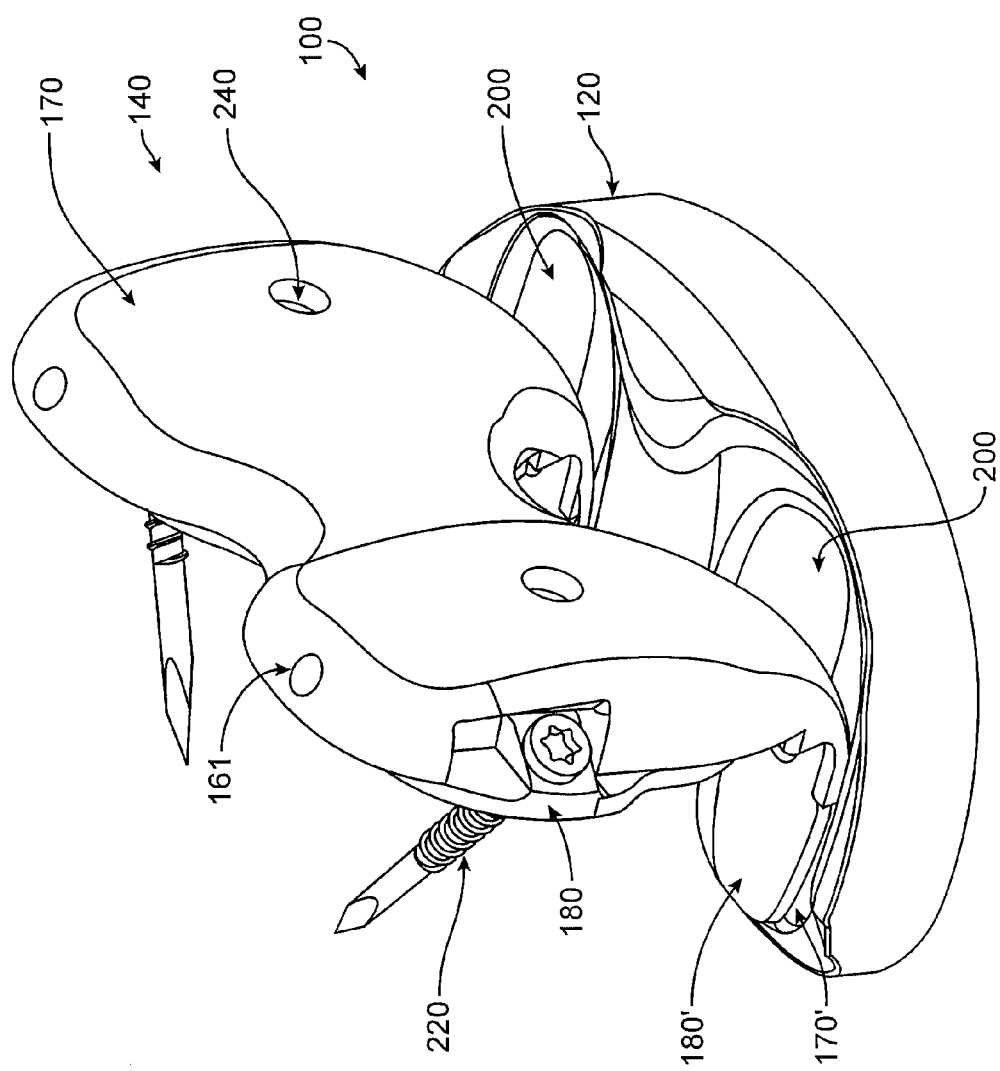
FIG. 3A is a front-perspective view of a knee balancing device according to one embodiment of the present invention.
Figure 3B:
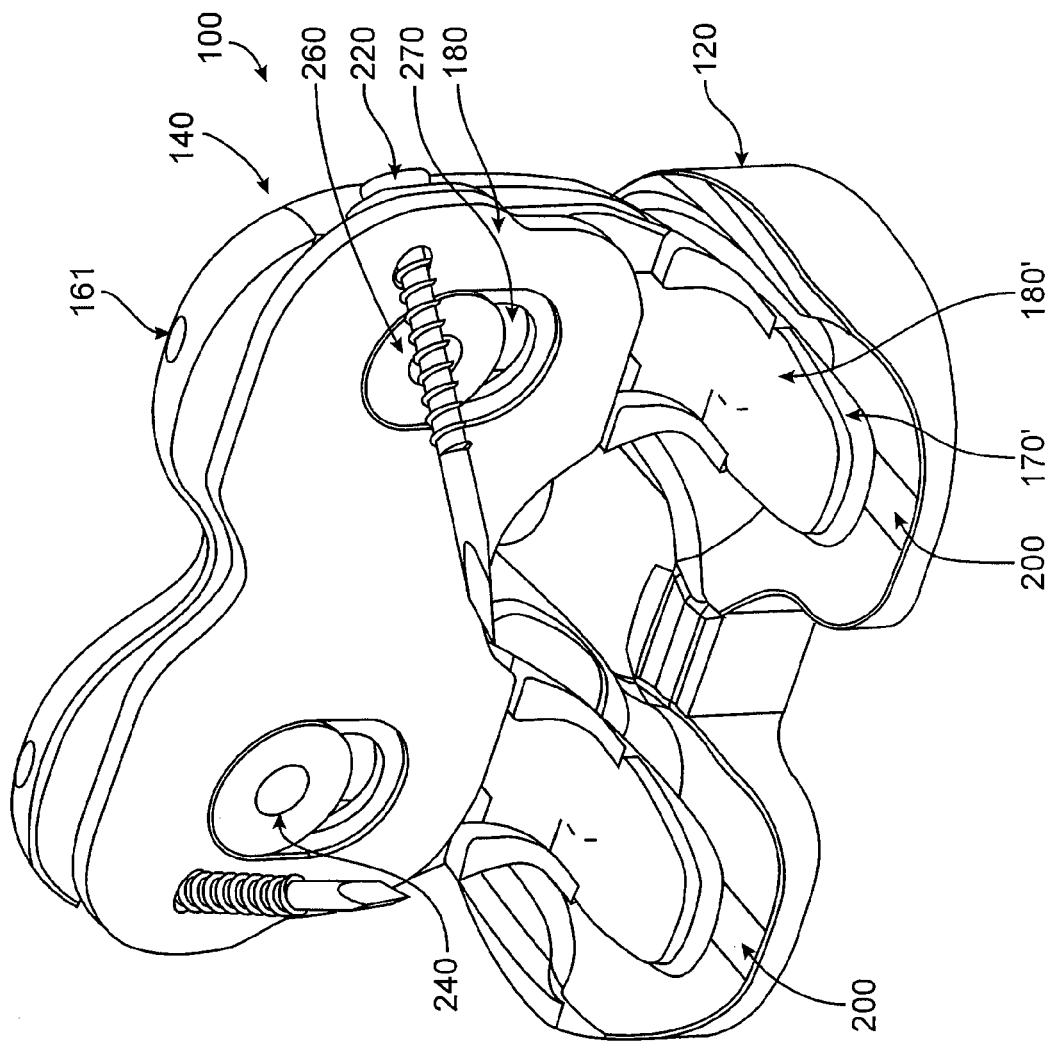
FIG. 3B is a rear-perspective view of the knee balancing device shown in FIG. 2A.

With reference now to FIGS. 3A and 3B, anterior and posterior perspective views, respectively, of an embodiment of a knee balancing system 100 are shown. Knee balancing system 100 suitably includes a femoral member 140 and a tibial member 120. Femoral member 140 may further include an adjustable femoral member 170 having adjustable posterior condylar members 170' and a stationary femoral member 180 having stationary posterior condylar members 180'. In some embodiments, adjustable femoral member 170 and adjustable posterior condylar member 170' will be one unitary piece or extrusion, while in other embodiments they may be two or more coupled pieces. Similarly, stationary femoral member 180 and stationary posterior condylar member 180' may comprise a one-piece construction or multiple pieces coupled together. In the embodiment shown, stationary femoral member 180 comprises a distal femoral plate coupled with two stationary posterior condylar members 180'. Any suitable configuration, combination or manufacturing process may be used in various embodiments.

Femoral member 140 may further include adjustment screw holes 161 for ingress/egress of adjustment screws (not shown), attachment screws 220, drill guide apertures 240, bushings 260, slots 270 and/or any other features described previously above. Tibial member 120 may suitably include two grooves 200 or depressions to provide for slidable coupling with femoral member 140. Generally, any of the features described above may be applied to knee balancing system 100.

Figure 3C:
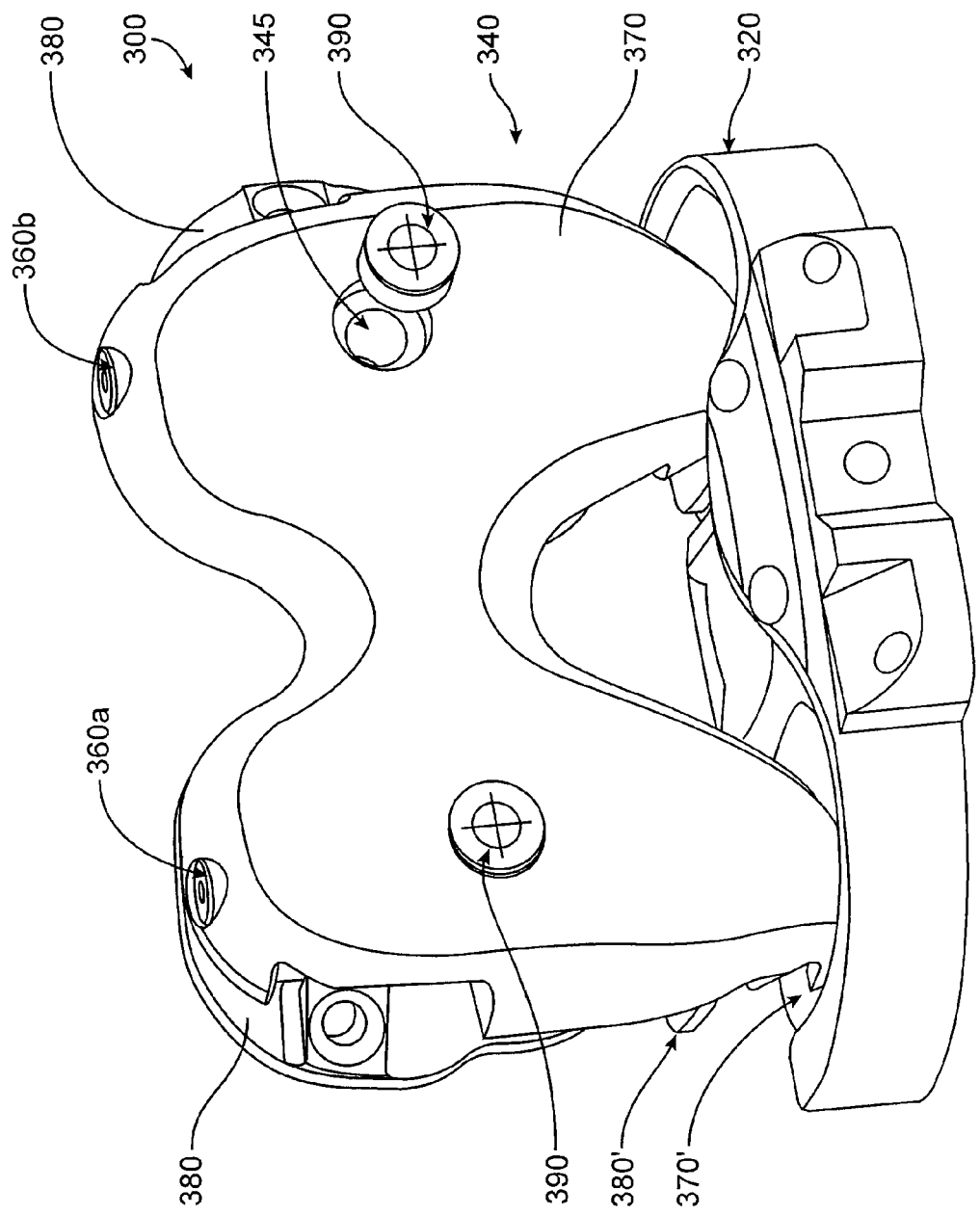
FIG. 3C is a front-perspective view a knee balancing device according to another embodiment of the present invention.

Referring now to FIG. 3C, a knee balancing system 300 similar to that described above is shown in frontal-perspective view. System 300 includes a tibial member 320 and a femoral member 340, the femoral member 340 including an adjustable member 370 coupled with a stationary member 380. Adjustable member 370 includes two adjustable posterior condylar members 370', and stationary member 380 includes two stationary posterior condylar members 380'. In FIG. 3C, one adjustment member 360a has been adjusted to move adjustable posterior condylar portion 370' away from stationary posterior condylar member 380' on that side, which would increase the height of the joint space on that side if the device were in a knee joint, and would also rotate adjustable femoral member 370 slightly relative to the distal femur. The pictured embodiment includes two apertures 345 as positioning features, and disposed within apertures 345 are two fiducials 390 (or markers, sensors or the like) for providing positional information to a computer navigation system or robotic surgery system. Such positional information, for example, may include a dynamically balanced orientation of the knee to make subsequent bone cuts on the femur F.

Figure 4B:
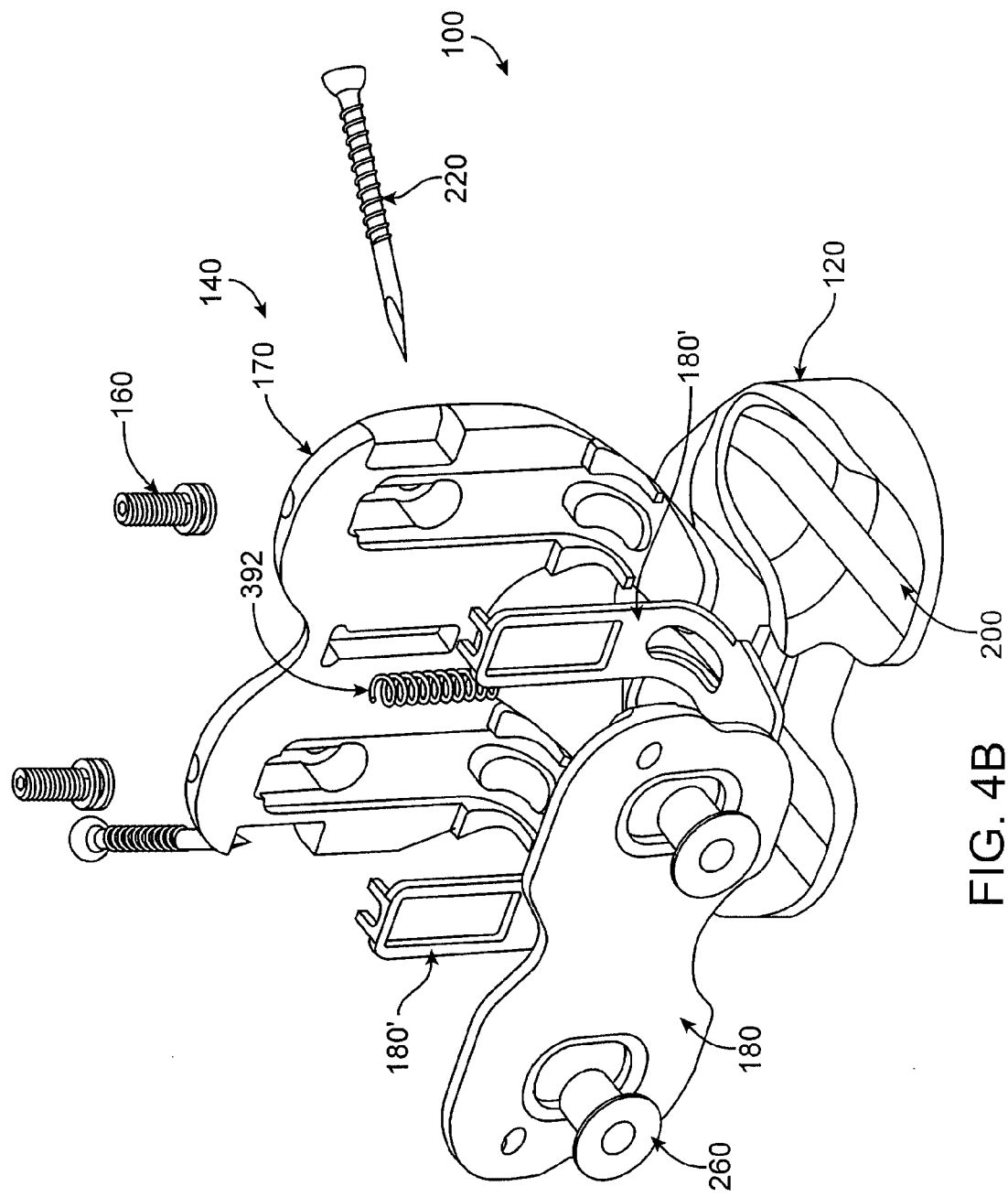
FIG. 4B is a rear-perspective, exploded view of the knee balancing device shown in FIG. 4A.

With reference now to FIGS. 4A and 4B, the embodiment of knee balancing system 100 from FIGS. 3A and 3B is shown in exploded view to more clearly show its component parts. In this embodiment, the component parts of knee balancing system 100 are the same as those shown and described above in reference to FIGS. 3A and 3B. It can be seen in FIGS. 4A and 4B that stationary femoral member 180 may comprise three coupled parts—a stationary femoral member distal plate 180 and two stationary posterior condylar members 180'. Such parts may be coupled by any suitable means, such as pressure fitting, sandwiching condylar members 180' between plate 180 and adjustable femoral member 170, screws, adhesives, and/or the like. Alternatively, stationary femoral member 180 may comprise one unitary piece or extrusion.

An additional part shown in FIG. 4B is a bias spring 392. Bias spring 392 may be incorporated into femoral member 140 to allow for rotation of adjustable femoral member 170 relative to stationary femoral member 180. Alternative embodiments of knee balancing system 100 may include any other suitable mechanism for allowing such rotation, anterior-posterior adjustment, and/or any other suitable adjustment(s).

In an exemplary method for enhancing a TKA procedure, a femoral member is typically removably engaged with a distal femur of a knee. Usually, the distal femur will have been cut to form a surface for engaging the femoral member, but this is not required in all embodiments. A tibial member is also engaged with a proximal tibia of the knee, usually a cut horizontal surface of the tibia. This tibial member may be provided as part of a dynamic knee balancing system or may be an off-the-shelf tibial trial insert, in various embodiments. In different embodiments, the tibial member may be placed before the femoral member or vice versa. In one embodiment, the femoral and tibial members are engaged with the femur and tibia while the knee is in full or nearly full extension, though in alternative embodiments they may be placed in flexion. The height, thickness, or overall shape of the tibial member may often be selected to provide a desired amount and balance of ligament tension while the knee is in extension.

Generally, the knee is then moved from extension to flexion, and the femoral member is adjusted to adjust tension in the MCL, LCL, posterior cruciate ligament and/or other ligaments to achieve a desired ligament balance in flexion. The knee may then be moved through a range of motion, and one or more subsequent adjustments may be made to the femoral member to adjust and balance ligament tension through the range of motion. Most, if not all, such adjustments and movements may, in some embodiments, be possible while the patella of the knee remains in approximately its normal anatomical position over the knee. This is advantageous because patellar tracking, an important determinant of knee function, may be assessed and adjusted during the TKA procedure. Typically, the goal of the surgeon will be to achieve dynamic balancing of ligament tension through the range of motion of the knee. Once this balancing is achieved with the femoral and tibial members in place, the positioning feature(s) on the adjustable femoral member provide positional information to a surgeon, computer, robotic system and/or the like, to help facilitate completion of the TKA procedure. Using this positional information, subsequent cuts (or drilling, burring or other shaping methods) are applied to the femur, with such cuts/shaping determining how the femoral prosthetic component of the artificial knee joint will be positioned and oriented on the distal femur. The femoral prosthetic component is then placed accordingly.

Figure 5:
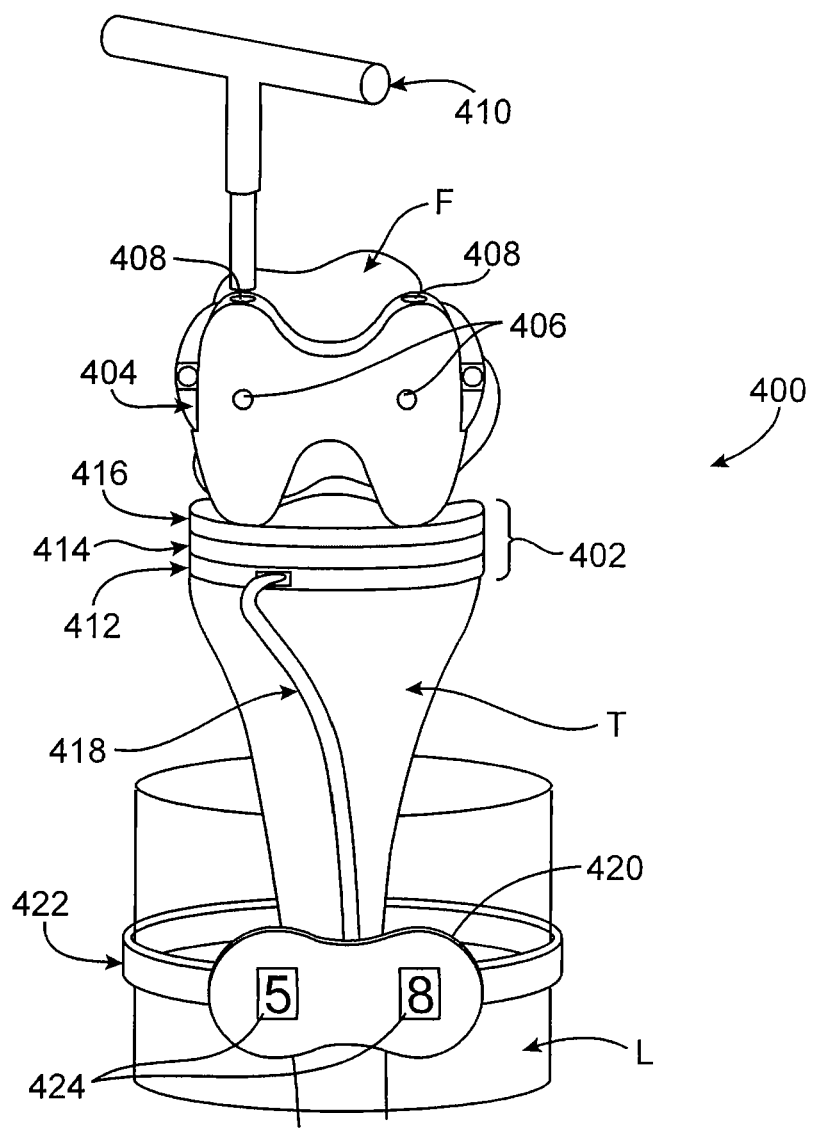
FIG. 5 is a front-perspective view of a knee balancing device with sensing capability, including a visual display and shown with an adjustment member for adjusting the femoral portion of the balancing device according to one embodiment of the present invention.

Referring now to FIG. 5, another embodiment of a knee surgery system 400 generally includes a tibial portion 402, an adjustable femoral portion 404, a visual display 420 and an adjustment tool 410 for adjusting femoral portion 404. Tibial portion 402, which is engaged with a proximal end of the tibia T, includes a sensor plate 412, an adaptor 414, and a tibial insert 416. Sensor plate 412 is coupled with visual display 420 via a cord 418. Visual display 420 includes two LED readouts 424 and a strap 422 for removably attaching visual display 420 to a patient's leg L. Femoral portion 402, which is engaged with a distal end of the femur F, includes two adjustment screws 408 and two positioning apertures 406. Aside from the sensing and visual display components and function, the general operation of tibial portion 402 and femoral portion 404 have been described in detail above.

Figure 6:
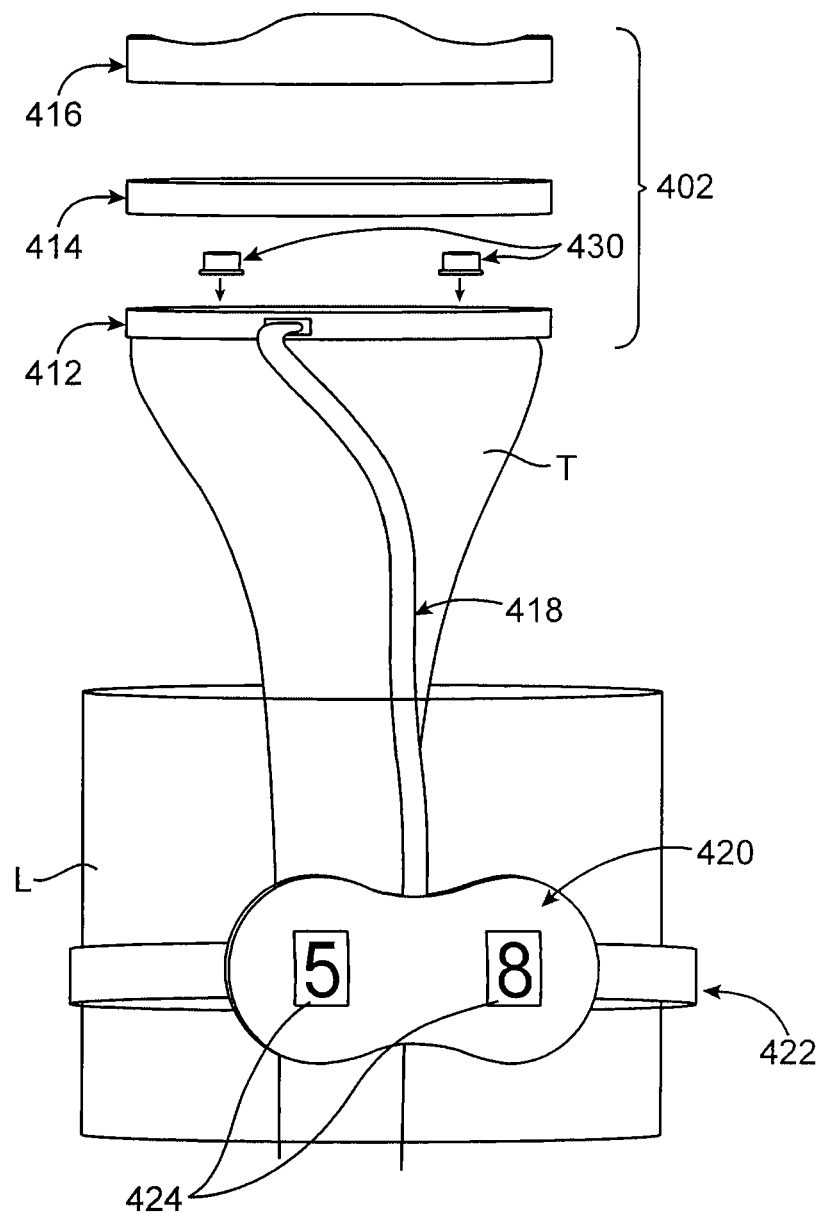
FIG. 6 is a front-perspective view of the tibial portion and visual display of the device of FIG. 5, with the tibial portion shown in exploded view.

With reference to FIG. 6, an exploded view of tibial portion 402 is shown. As illustrated, in some embodiments, sensor plate 412 acts as a housing for one or more sensors 430. Sensors 430 may be any suitable force or pressure sensors, such as but not limited to piezoelectric sensors, force sensing resistors, strain gauges, load cells or the like. In some embodiments, two sensors 430 are used, in order to sense pressure on medial and lateral sides of the knee. In other embodiments, only one sensor 430 may be used, more than two sensors 430 may be used, sensors 430 may be coupled with both tibial portion 402 and femoral portion 404 and/or the like. In one alternative embodiment, for example, sensor plate 412 itself is one large pressure sensor 430, rather than a housing for sensors 430. Any suitable combination, shape, size and configuration of pressure and/or force sensors is contemplated.

Adaptor 414 is generally a plate coupled with sensor plate 412 and adapted to couple sensor plate 412 with tibial insert 416. Typically, adaptor plate 414 is removably couplable with tibial insert 416, such that multiple, differently-sized inserts 416 may be tried in the knee during a surgical procedure, while using the same sensor plate 412 and adaptor 414. In some embodiments, such as the one shown in FIG. 6, adaptor 414 and sensor plate are two pieces attached together. In alternative embodiments, a one-piece plate may be used to house sensors 430 and to couple with tibial inserts 416. In yet another embodiment, all of tibial portion 402 may be one piece. Furthermore, it is not required that sensor plate 412 be located in contact with the tibia T. In an alternative embodiment, for example, sensor plate 412 may be disposed within a tibial insert 416 so as not to contact the tibia T. In the embodiment shown, sensors 430 are embedded in sensor plate 412, and adaptor 414 is attached to sensor plate 412 via adhesive, welding or any other suitable method.

As previously mentioned, sensors 430 may comprise any of a number of suitable pressure and/or force sensors. In one embodiment, a known voltage is transmitted to sensors 430, the voltage passing out of sensors 430 is measured, and a percentage of the voltage leaving sensors 430 to the known voltage is calculated. From this percentage, pressure is derived. An analog signal representing the pressure is converted to a digital signal with an analog-to-digital (A/D) converter, and the A/D converter provides the digital signal to a look-up table that determines a display value (or values) representing the pressure (or force). A user may use the display value as an absolute number and/or may move the knee and compare pressure values at flexion and extension. The A/D converter, as well as any additional processing modules for processing sensed data into usable data may all be housed in a processor (not shown). The processor, in turn, may be housed in sensor plate 412 or in visual display 420. Alternative methods for sensing and displaying sensed data are also contemplated.

Sensor plate 412 is coupled with visual display 420 via cord 418, or alternatively via one or more other connection devices. In alternative embodiments, for example, sensor plate 412 may be coupled with visual display 420 via wireless infrared, electromagnetic, optical or other remote, wireless connection(s). In various embodiments, sensors 430 themselves may be coupled with visual display 420, or alternatively, sensors may be coupled with a processor housed in sensor plate 412, and the processor (not shown) may then be coupled with visual display 420 via cord 418 or other means. Visual display 420 itself may be attached directly to sensor plate 412 or may be separate from sensor plate 412, as shown. In various embodiments, visual display 420 may be coupled with the lower leg L or the thigh (not shown) of a patient via a strap 422 or other coupling means. As stated previously, visual display 420 may house a processor for processing sensed data transmitted from sensors 430 into usable data for displaying on LED readouts 424 or other display means.

Figure 7:
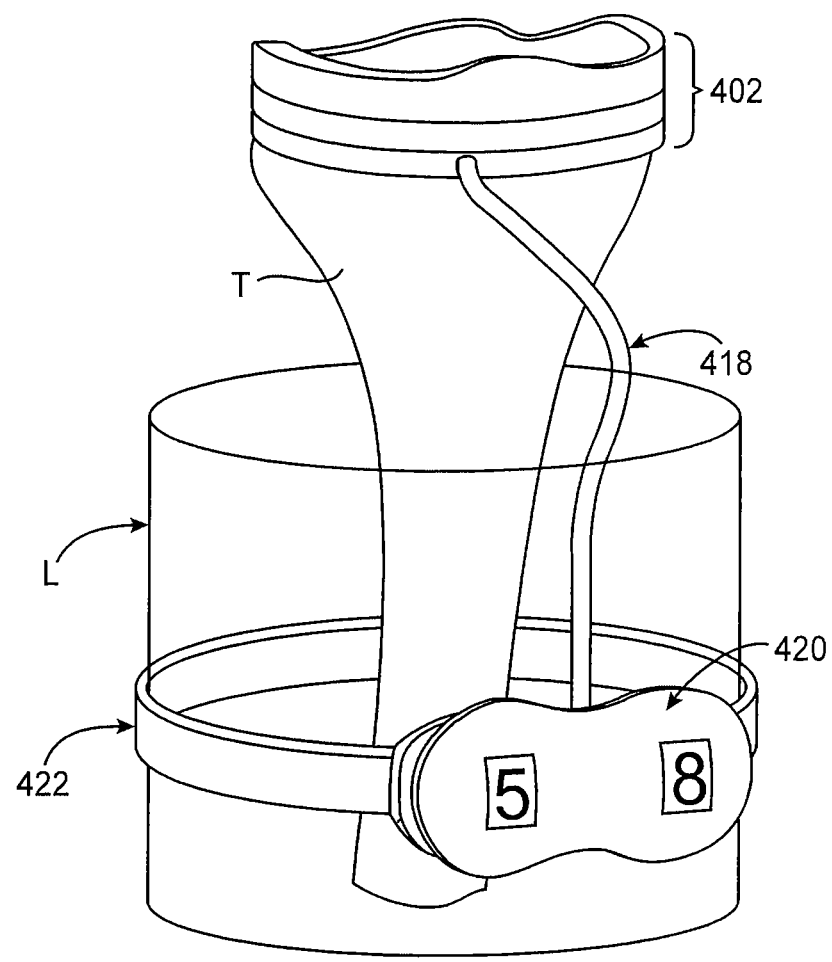
FIG. 7 is a superior, angled perspective view of the tibial portion and visual display of FIGS. 5 and 6.

FIG. 7 is an angled, perspective view of tibial portion 402 and other tibial components of system 400, as in FIGS. 5 and 6.

Figure 8:
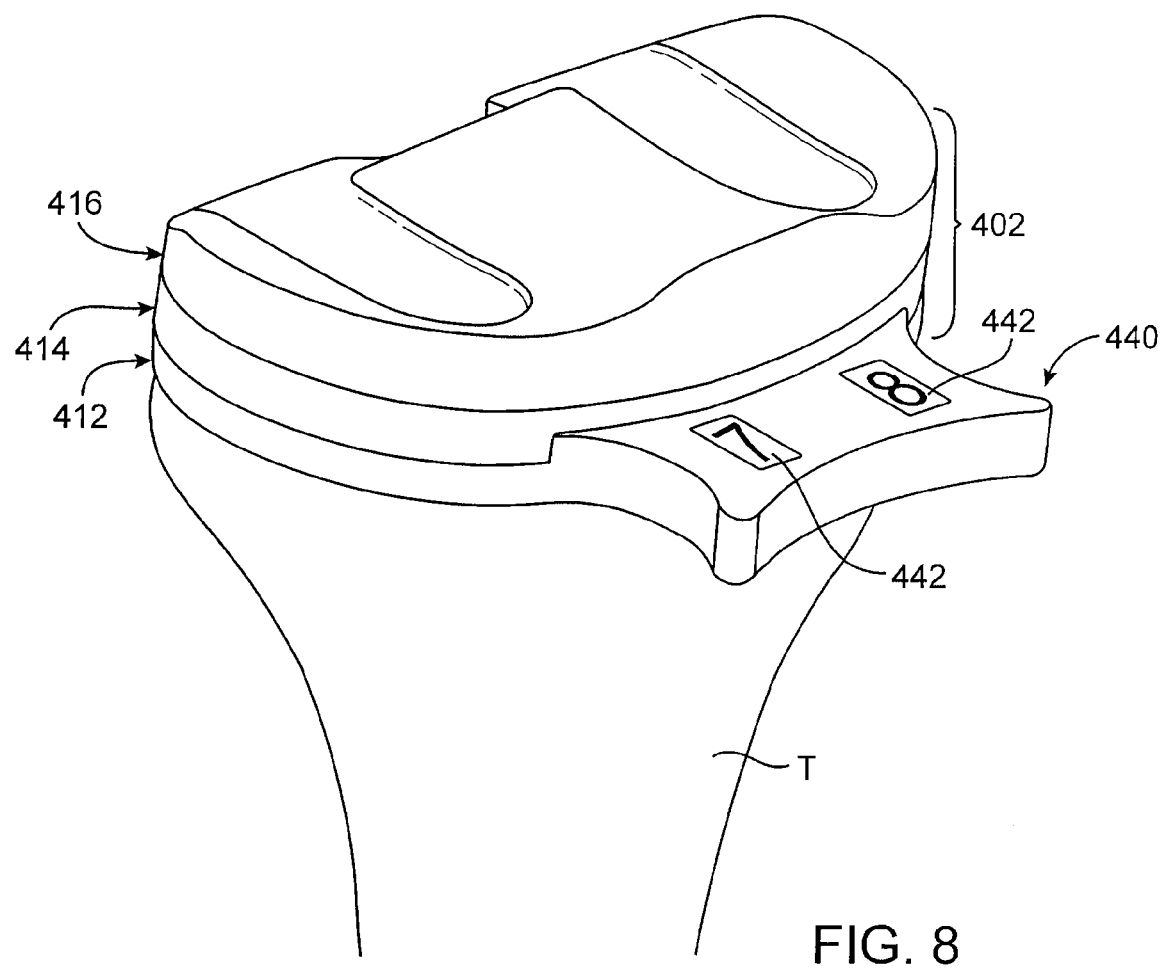
FIG. 8 is a perspective view of a tibial portion of a knee balancing device with sensing capability coupled with a visual display according to an alternative embodiment of the invention.

An alternative embodiment is shown in FIG. 8. As illustrated, tibial portion 402 may in some embodiments be attached to an immediately adjacent visual display 440 having multiple LED readouts. Either the sensors, the processor (neither are visible) or both are coupled with visual display 440. In some embodiments, visual display 440 is coupled with both sensor plate 412 and adaptor 414. Generally, visual display 440 may have any suitable size, shape and overall configuration and may be positioned in any appropriate location, relative to the rest of system 400.

It is contemplated that any of the devices, systems and methods described above may be incorporated with any suitable knee surgery procedures or systems currently used or discovered in the future. For example, inventive devices, systems and methods may be readily incorporated with any number of different visualization, navigation and/or robotic systems for performing a knee surgery, such as image-guided systems for performing, planning or enhancing a TKA procedure, robotic surgery systems such as the da Vinci® Surgical System provided by Intuitive Surgical, Inc. (Sunnyvale, Calif.), or the like. Any suitable imaging or visualization modality and technique may be used with various embodiments of the devices, systems and methods of the invention, such as but not limited to infrared or ultrasound imaging. Many suitable modifications and additions to the devices described above may also be made without departing from the scope of the invention.

Therefore, while the foregoing is a complete and accurate description of exemplary embodiments of the present invention, various embodiments of the devices, systems and methods described may include any number of modifications and additions. The exemplary descriptions above should thus not be interpreted to limit the scope of the invention as it is defined in the appended claims.

What is claimed is:

1. A device for performing a surgical procedure on a knee joint, comprising:
   a sensor plate for removable placement within the knee joint during the surgical procedure;
   a plurality of sensors disposed within the sensor plate and configured to sense force or pressure on medial and lateral sides of the knee joint;
   a processor coupled to the plurality of sensors and configured to process sensed force or pressure data into usable data; and
   a visual display coupled to the processor and including separate individual medial and lateral readouts, each readout in the form of a single value expressed by one or more numerical digits, the medial readout being configured to display the usable data as a numeric representation of the sensed force or pressure on the medial side of the knee joint, the lateral readout being configured to display the usable data as a numeric representation of the sensed force or pressure on the lateral side of the knee joint.

2. The device of claim 1, further comprising:
   a femoral portion couplable to a distal end of a femur; and
   a tibial portion couplable to a proximal end of a tibia, wherein the sensor plate is couplable to or integrated with the femoral portion or the tibial portion.

3. The device of claim 2, wherein the femoral portion includes at least one positioning feature providing positional information for facilitating the surgical procedure.

4. The device of claim 3, wherein the positioning feature is configured to orient at least one of a cutting guide, a surgical saw blade, a bur, a mill, a surgical navigation system, or a robotic surgical system.

5. The device of claim 3, wherein the positioning feature comprises at least one of an aperture, a drill bit guide, a surface marker, a surface feature, a measurement device, an embedded marker, a fiducial marker, a transponder, a transceiver, or a sensor.

6. The device of claim 3, wherein the positioning feature includes a plurality of apertures extending through the femoral portion.

7. A device for performing a surgical procedure on a knee joint, comprising:
a sensor plate for removable placement within the knee joint during the surgical procedure,
a plurality of sensors disposed within the sensor plate and configured to sense force or pressure on medial and lateral sides of the knee joint;
a processor coupled to the plurality of sensors and configured to process sensed force or pressure data into usable data;
a visual display coupled to the processor and including individual medial and lateral readouts, the medial and lateral readouts, each readout in the form of a single value expressed by one or more numerical digits being configured to display the usable data as a visual representation of the sensed force or pressure on the medial and lateral sides of the knee joint, respectively;
a femoral portion couplable to a distal end of a femur, the femoral portion including at least one positioning feature providing positional information for facilitating the surgical procedure, the at least one positioning feature including a plurality of apertures extending through the femoral portion; wherein at least one of the apertures, in the plurality of apertures, includes a bushing that moves along a slot in the femoral portion as the femoral portion is adjusted; and
a tibial portion couplable to a proximal end of a tibia, wherein the sensor plate is couplable to or integrated with the femoral portion or the tibial portion.

8. The device of claim 1, wherein the medial and lateral readouts include a medial LED readout and a lateral LED readout.

9. The device of claim 1, wherein at least two of the plurality of sensors are disposed on opposite sides of the sensor plate, including one sensor on the medial side of the knee joint, during use, and one sensor on the lateral side of the knee joint, during use.

10. The device of claim 1, wherein, during use, the sensor plate is disposed at a proximal end of a tibia.

11. A device for performing a surgical procedure on a knee joint, comprising:
a sensor plate for removable placement within the knee joint during the surgical procedure;
a plurality of force or pressure sensors disposed within the sensor plate and configured to sense force or pressure on medial and lateral sides of the knee; and
a visual display wirelessly coupled to the plurality of sensors and including separate individual medial and lateral readouts, each readout in the form of a single value expressed by one or more numerical digits, the medial readout being configured to display the sensed force or pressure on the medial side of the knee joint as a numeric representation, the lateral readout being configured to display the sensed force or pressure on the lateral side of the knee joint as a numeric representation.

12. The device of claim 11, further comprising:
a femoral portion couplable to a distal end of a femur; and
a tibial portion couplable to a proximal end of a tibia,
wherein the sensor plate is couplable to or integrated with the femoral portion or the tibial portion, and
wherein the femoral portion includes at least one positioning feature providing positional information for facilitating the surgical procedure.

13. The device of claim 11, wherein the medial readout and the lateral readout comprise respective medial and lateral LED readouts.

14. The device of claim 11, wherein at least two of the plurality of force or pressure sensors are disposed on opposite sides of the sensor plate, including one sensor on the medial side of the knee joint, during use, and one sensor on the lateral side of the knee joint, during use.

15. A device for performing a surgical procedure on a knee joint, comprising:
a tibial portion couplable to a proximal end of a tibia;
a femoral portion couplable to a distal end of a femur, the femoral portion including a plurality of apertures extending through the femoral portion;
a sensor plate for removable placement within the knee joint during the surgical procedure, the sensor plate being couplable to or integrated with the femoral portion or the tibial portion;
a plurality of sensors disposed within the sensor plate and configured to sense force or pressure on medial and lateral sides of the knee joint, at least two of the plurality of sensors being disposed on opposite sides of the sensor plate, including one sensor on the medial side of the knee joint, during use, and one sensor on the lateral side of the knee joint, during use;
a processor coupled to the plurality of sensors and configured to process sensed force or pressure data into usable data; and
a visual display coupled to the processor and including separate individual medial and lateral LED readouts, each readout in the form of a single value expressed by one or more numerical digits, the medial LED readout being configured to display the usable data as a numeric representation of the sensed force or pressure on the medial side of the knee joint, the lateral LED readout being configured to display the usable data as a numeric representation of the sensed force or pressure on the lateral side of the knee joint.

16. A device for performing a surgical procedure on a knee joint, comprising:
a tibial portion couplable to a proximal end of a tibia;
a femoral portion couplable to a distal end of a femur, the femoral portion including a plurality of apertures extending through the femoral portion;
a sensor plate for removable placement within the knee joint during the surgical procedure, the sensor plate being couplable to or integrated with the femoral portion or the tibial portion;
a plurality of sensors disposed within the sensor plate and configured to sense force or pressure on medial and lateral sides of the knee joint, at least two of the plurality of sensors being disposed on opposite sides of the sensor plate, including one sensor on the medial side of the knee joint, during use, and one sensor on the lateral side of the knee joint, during use;

a processor coupled to the plurality of sensors and configured to process sensed force or pressure data into usable data; and a visual display coupled to the processor and including separate medial and lateral LED readouts, each readout in the form of a single value expressed by one or more numerical digits, the medial and lateral LED readouts being configured to display the usable data as a visual representation of the sensed force or pressure on the medial and lateral sides of the knee joint, respectively;

wherein at least one of the apertures, in the plurality of apertures, includes a bushing that moves along a slot in the femoral portion as the femoral portion is adjusted.

17. The device of claim 15, wherein, during use, the sensor plate is disposed at the proximal end of the tibia.

18. The device of claim 15, wherein the visual display further comprises a strap for removably attaching the visual display to a patient's leg.

19. The device of claim 15, wherein the visual display is physically coupled to the sensor plate.

20. The device of claim 1, wherein the visual display further comprises a strap for removably attaching the visual display to a patient's leg.

21. The device of claim 1, wherein the visual display is physically coupled to the device for performing the surgical procedure.

22. The device of claim 11, wherein the visual display further comprises a strap for removably attaching the visual display to a patient's leg.

23. The device of claim 11, wherein the visual display is physically integrated into the device for performing the surgical procedure.

* * * * *

UNITED STATES PATENT AND TRADEMARK OFFICE
CERTIFICATE OF CORRECTION

PATENT NO. : 9,572,588 B2  
APPLICATION NO. : 13/709506  
DATED : February 21, 2017  
INVENTOR(S) : Fisher et al.

Page 1 of 1

It is certified that error appears in the above-identified patent and that said Letters Patent is hereby corrected as shown below:

On the Title Page

In item (54), and in the Specification, Column 1, Line 1-2, in "Title" after "WITH", delete "FORCE OR"

In the Claims

In Column 17, Line 21, in Claim 7, delete "procedure," and insert --procedure;-- therefor In Column 17, Line 58, in Claim 11, after "joint,", delete "¶"

Signed and Sealed this  
Twenty-fourth Day of April, 2018

Andrei Iancu  
*Director of the United States Patent and Trademark Office*